(12) United States Patent
Fitzgerald et al.

(10) Patent No.: US 10,463,141 B2
(45) Date of Patent: Nov. 5, 2019

(54) WEARABLE MODULAR ELECTRONIC DEVICE, SUCH AS TO HOLD A SELECTABLE AND/OR REPLACEABLE BIOMETRIC SENSOR IN CLOSE PROXIMITY TO AND/OR IN PHYSICAL CONTACT WITH A WEARER AND/OR TO HOLD A BATTERY

(71) Applicant: Blingtec, Inc., Boston, MA (US)

(72) Inventors: Heloisa Fitzgerald, Boston, MA (US); Warren Katz, Boston, MA (US); Sean Batir, Boston, MA (US); Catherine Koch, Boston, MA (US)

(73) Assignee: Heloisa Fitzgerald Jewelry, Westwood, MA (US)

( * ) Notice: Subject to any disclaimer, the term of this patent is extended or adjusted under 35 U.S.C. 154(b) by 169 days.

(21) Appl. No.: 14/789,869

(22) Filed: Jul. 1, 2015

(65) Prior Publication Data

US 2016/0029778 A1    Feb. 4, 2016

Related U.S. Application Data

(60) Provisional application No. 62/019,429, filed on Jul. 1, 2014.

(51) Int. Cl.
*A45F 5/02* (2006.01)
*A45F 5/00* (2006.01)
*A45C 15/00* (2006.01)

(52) U.S. Cl.
CPC ............... *A45F 5/02* (2013.01); *A45C 15/00* (2013.01); *A45F 5/00* (2013.01); *A45F 5/021* (2013.01);

(Continued)

(58) Field of Classification Search
CPC ....... A44C 5/24; A44C 5/246; Y10T 24/4016; Y10T 24/4782; Y10T 24/2155

(Continued)

(56) References Cited

U.S. PATENT DOCUMENTS

| 4,938,228 A | * | 7/1990 | Righter ............... A61B 5/0245 600/503 |
| 6,192,253 B1 | * | 2/2001 | Charlier ............... H04B 1/385 455/340 |

(Continued)

FOREIGN PATENT DOCUMENTS

FR    2683982    * 11/1991

*Primary Examiner* — Adam J Waggenspack
(74) *Attorney, Agent, or Firm* — Garrett IP

(57) ABSTRACT

A wearable modular electronic device to maintain an electronic module proximate to a wearer may be configured to attach to a wearable accessory such as, without limitation jewelry (e.g., necklace/pendant, finger ring, earring, body piercing, brooch, wrist bracelet, and/or wristwatch), a money clip, a belt buckle, a handbag, and/or an article of clothing. A wearable modular electronic device may be configured as a clasp assembly for a wristwatch, which may be configured to replace an existing clasp of a wristwatch, and which may be configurable for multiple types of wristbands (e.g., strap-type and/or metal). An electronic module may include a battery and/or sensor, such as a biometric sensor, and the wearable modular electronic device or a surface thereof may be contoured to coincide with a body part of a wearer and/or otherwise configured to maintain the biometric sensor proximate to the wearer.

15 Claims, 33 Drawing Sheets

(52) U.S. Cl.
CPC ... *A45F 2005/002* (2013.01); *A45F 2005/008* (2013.01); *A45F 2005/023* (2013.01); *A45F 2200/0516* (2013.01)

(58) Field of Classification Search
USPC .................. 224/164, 174, 176; 24/265 WS
See application file for complete search history.

(56) References Cited

U.S. PATENT DOCUMENTS

| | | | | |
|---|---|---|---|---|
| 6,493,908 | B2* | 12/2002 | Thalheim | A44C 5/24 24/265 B |
| 7,509,712 | B2* | 3/2009 | Sima | A44C 5/147 24/265 WS |
| 9,152,129 | B2* | 10/2015 | Modaragamage | A44C 5/24 |
| 9,560,900 | B2* | 2/2017 | Pier | A44C 5/246 |
| 2005/0237864 | A1* | 10/2005 | Albisetti | A44C 5/22 368/282 |
| 2009/0054751 | A1* | 2/2009 | Babashan | A61B 5/0002 600/324 |

* cited by examiner (end view)

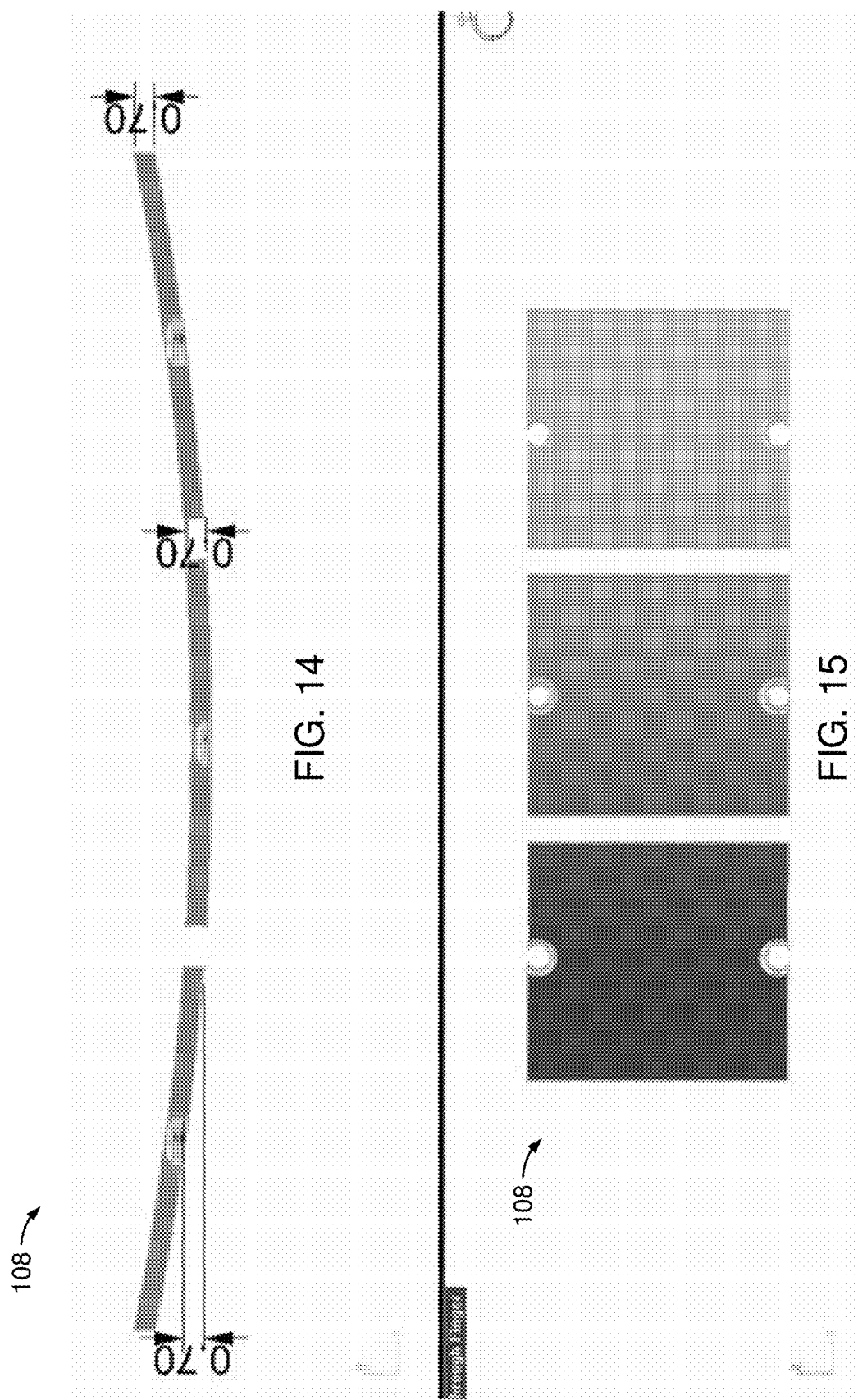

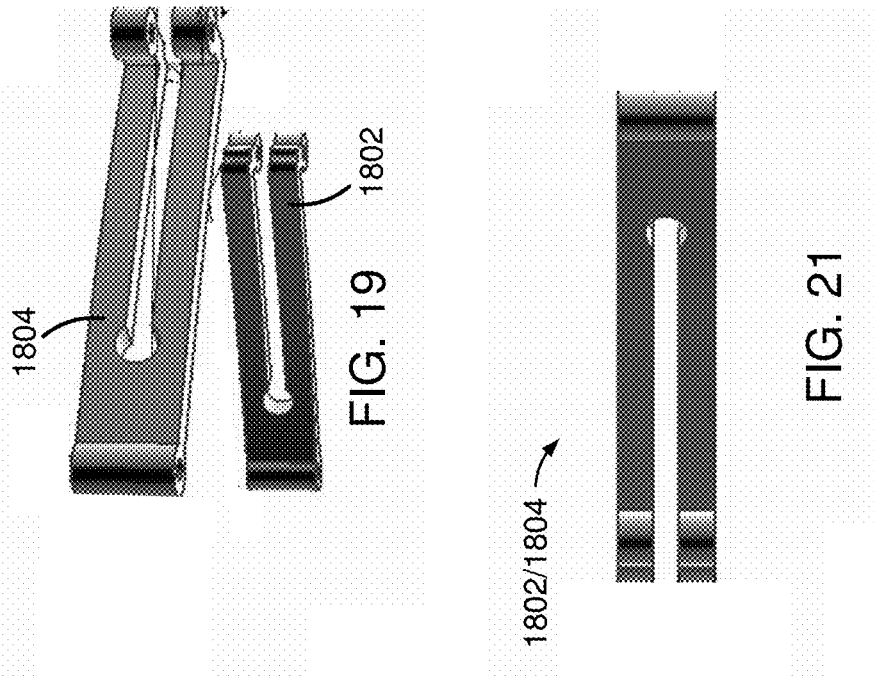
FIG. 19
FIG. 21
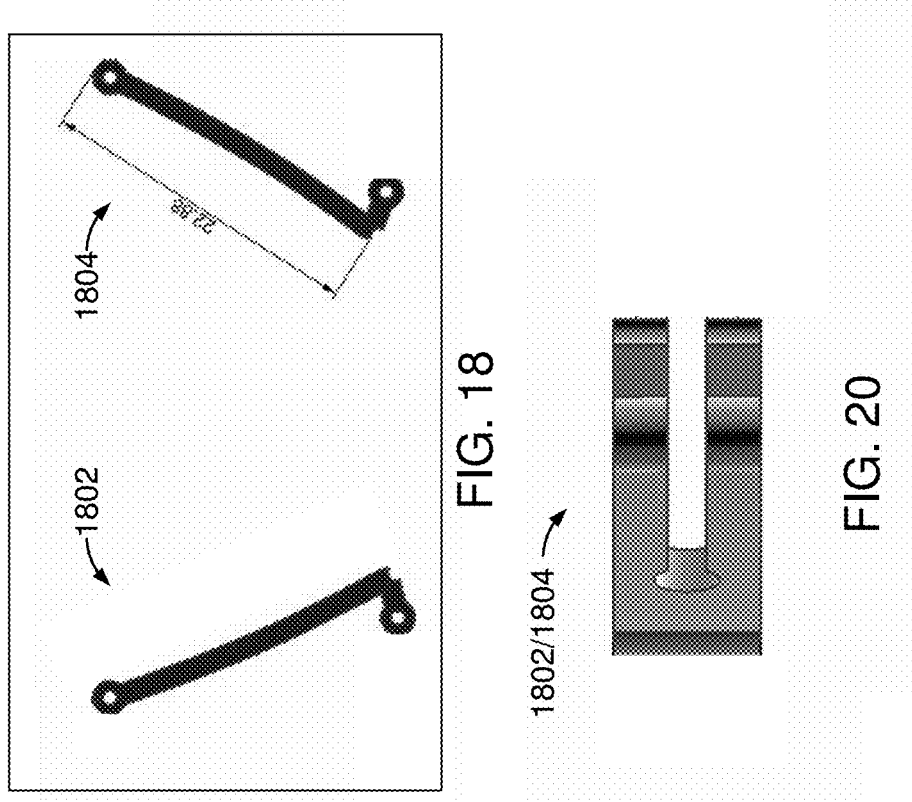
FIG. 18
FIG. 20

4000

WEARABLE MODULAR ELECTRONIC DEVICE, SUCH AS TO HOLD A SELECTABLE AND/OR REPLACEABLE BIOMETRIC SENSOR IN CLOSE PROXIMITY TO AND/OR IN PHYSICAL CONTACT WITH A WEARER AND/OR TO HOLD A BATTERY

CROSS REFERENCE TO RELATED APPLICATIONS

This application claims the benefit of U.S. Provisional Patent Application No. 62/019,429, filed Jul. 1, 2014, which is incorporated herein by reference in its entirety.

TECHNICAL FIELD

Modular wearable technology; smart watches; wristband clasps; modular electronic assemblies; and sensors, including biometric sensors.

BACKGROUND

The term "wearable technology" refers to clothing and wearable accessories that incorporate electronic features or devices, such as a smart-watch or smartwatch.

A smart-watch is a computerized wristwatch with functionality beyond timekeeping. Early smart-watches can perform basic tasks, such as calculations, translations, and game playing. More-recent smart-watches can run mobile applications (mobile apps), and some can reportedly run a mobile operating system and function as a portable media player. Development of smart-watches with mobile telephone capability (i.e., "watch-phones") can be expected.

Wearable technology is often designed with a focus on "hip" or "high-tech" fashion trends, which may not appeal to wearers of elegant clothing and accessories.

BRIEF DESCRIPTION OF THE DRAWINGS

For illustrative purposes, one or more features disclosed herein may be presented and/or described by way of example and/or with reference to one or more drawing figured listed below. Methods and systems disclosed herein are not, however, limited to such examples or illustrations.

FIG. 14 is a side-view illustration of cover for the container of FIG. 1.

FIG. 15 is a perspective the covers of FIG. 17.

FIG. 18 is a side-view illustration of arms, such as illustrated in FIG. 4.

FIG. 19 is a perspective illustration of the arms of FIG. 21.

FIG. 20 is a perspective illustration of an arm of FIG. 21.

FIG. 21 is another perspective illustration of the arm of FIG. 23.

Figure 1:
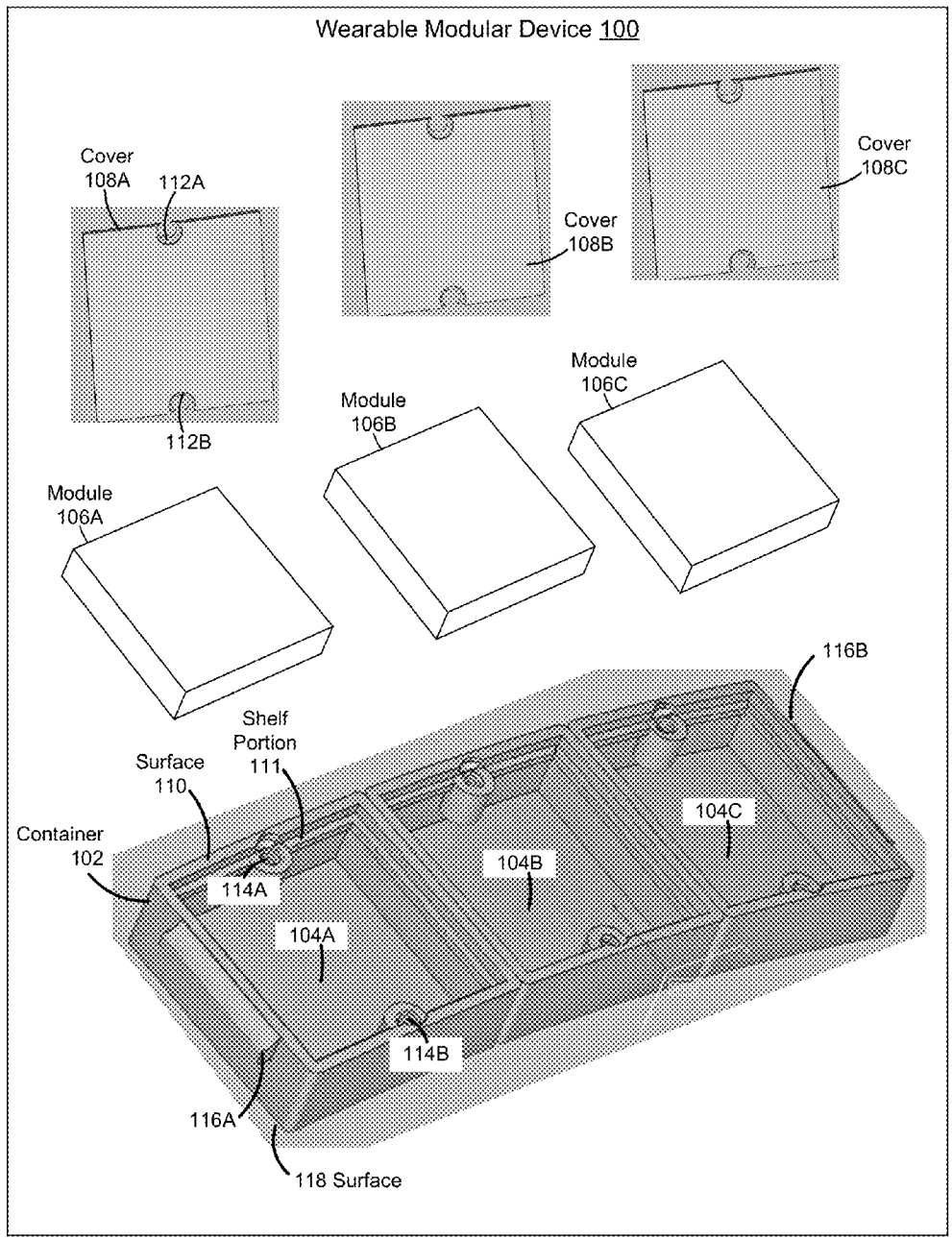
FIG. 1 is a perspective view of a wearable modular device that includes a container having cavities to receive one or more modules.

In the drawings, the leftmost digit(s) of a reference number identifies the drawing in which the reference number first appears.

DETAILED DESCRIPTION

FIG. 1 is a perspective view of a wearable modular device 100 that includes a container 102 having cavities 104 to receive modules 106.

In the example of FIG. 1, container 102 includes three cavities 104 to hold three respective modules 106. Device 100 is not, however, limited to this example. Container 102 may, for example, be configured to hold a single module 106 or more than one module 106.

A module 106 may be include an electrical and/or electro-mechanical system, such as described below with reference to FIG. 2, and/or a battery, such as to provide electrical power to another device or system (e.g., to provide electrical power to another module 106).

Where container 102 is configured to hold multiple modules 106, two more modules 106 may be configured to perform similar functions and/or functions that differ from one another.

Device 100 further includes covers 108 to enclose cavities 104. In FIG. 1, walls of cavities 104 include shelf portions 111, and covers 108 are configured to rest on shelf portions 111. Container 102 and a cover 108 may be configured such that, when the cover 108 is positioned on shelf portion 108, a surface 109 of the cover 108 is in a same plane as a surface 110 of container 102.

A cover 108 may be affixed or fastened to container 100 with one or more techniques.

Container 102 and a cover 108 may be configured to provide a watertight or substantially watertight seal with respect to a cavity 104.

A cover 108 may be permanently affixed to container 102 after a module 106 is placed with a respective cavity 104. Alternatively, a cover 108 may be removable from container 102, such as to permit reconfiguration of device 100 (e.g., to permit replacement of a module 106 within a cavity 104 with another module 106). A replacement module and a replaced module 106 may be configured to perform similar functions and/or functions differ between the modules.

In the example of FIG. 1, covers 108 include openings 112, and container 102 includes corresponding threaded cavities 114 to permit covers 108 to be secured to container 102 with threaded screws. Device 100 is not, however, limited to this example. In another embodiment, container 102 is configured to permit removal of a cover 108 without tools, such as by unsnapping a deformable portion of a clasp to release a module 106 (e.g., to release an electrical and/or electro-mechanical system, or a battery).

Device 100 may be configured to attach to an article of clothing and/or a wearable accessory. In the example of FIG. 1, container 100 includes protrusions 116 to permit device 100 to be secured to a wearable accessory, examples of which are provided further below.

Device 100 may be configured such that, when attached to a wearable accessory, a surface of device 100 is in direct contact with a wearer. A surface of device 100 may have opening therethrough to a portion of module 106 to contact a wearer and/or permit module 106 to more-directly sense a biometric feature of the wearer.

Device 100 may be configured such that, when attached to a wearable accessory, a surface of device 100 is in direct contact with a wearer.

Device 100 and/or a surface thereof may be shaped or contoured based on a shape or contour of the wearer. In FIG. 1, a surface 118 of container 102 has a concave contour, which may correspond to a convex contour of a human wrist. Surface 110 of container 102, and covers 108 may have a similar contour as surface 108. Device 100 is not, however, limited to these examples.

Figure 2:
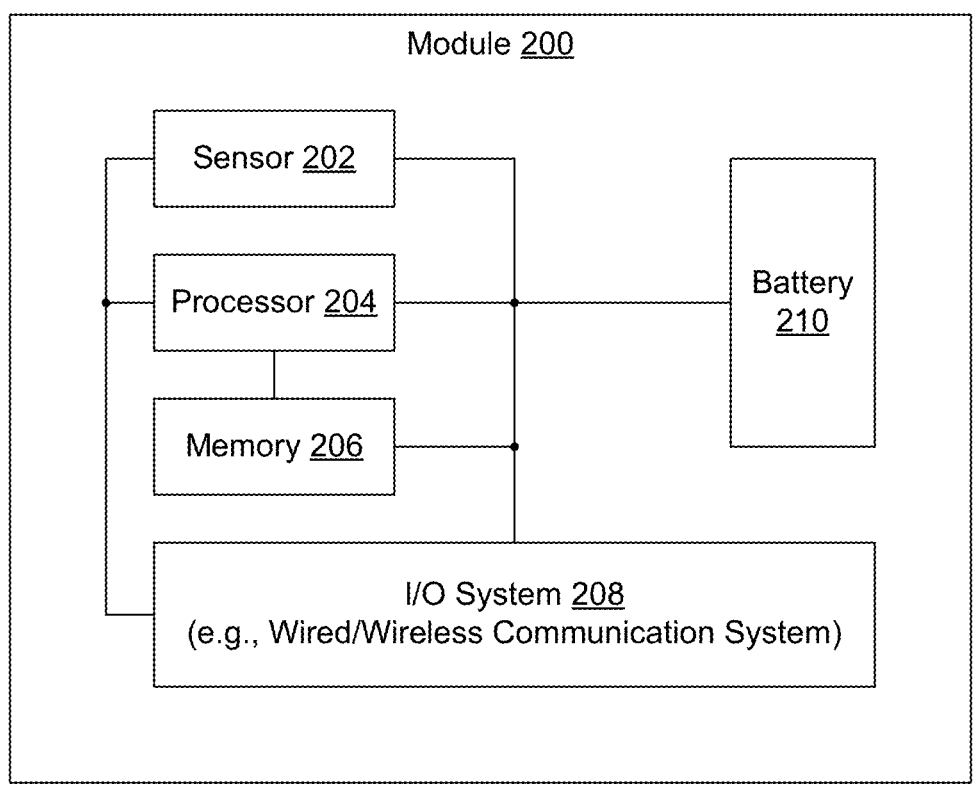
FIG. 2 is a block diagram of an example module.

FIG. 2 is a block diagram of a module 200 that includes one or more sensors, illustrated here as a sensor 202. Sensor 202 may be configured to sense one or more environmental conditions and/or biometric features, characteristics, and/or traits of a user. Sensor 202 may be further configured to output an indication (e.g., an analog signal or digital data) of a sensed feature or condition.

Module 200 may include a micro-electromechanical system (MEMS), which has components of between 1 to 100 micrometers ($\mu$m) in size, and which may include microprocessor and a sensor.

Container 102 and/or surface 118 may be made of a material based on sensor 202, such as to permit sensor 202 to sense of a feature or condition through surface 118.

Module 200 further includes an instruction processor 204, and a computer readable medium, illustrated here as memory 206, to store instructions to be executed by processor 204. The instructions may include instructions to cause processor 204 to process indications output from sensor 202. The instructions may include instructions to cause processor 204 provide controls and/or data to sensor 202. Memory 206 may be further configured to store data to be used by processor 204 and/or data generated by processor 204.

Module 200 further includes an input/output (I/O) system 208 to communicate between an external device and one or more of sensor 202 and processor 204, such as to provide information from sensor 202 and/or processor 204 to the external device, and/or to receive instructions, updates, and/or controls/commands from the external device.

I/O system 208 may include a wired and/or wireless communication system (e.g., Bluetooth, Wi-Fi, and/or GPS).

I/O system may be configured to communicate over a packet-based network, such as the Internet. I/O system 208 may, for example, include a wireless network interface controller (NIC) to communicate with an access point of a packet-based network over a wireless channel.

I/O system may be configured to communicate with a local device (i.e., a device that is physical proximate to module 200. The local device may include another module 200 and/or a user device (e.g., a personal computer/laptop/pad, mobile telephone, smartphone, and/or smartwatch).

I/O system 208 may, for example, be configured to communicate based on a standardized and/or proprietary communication protocol/format.

In FIG. 2, module 200 further includes an electrical power source, illustrated here as a battery 210. In an embodiment, if battery 210 runs out of charge, module 200 may be replaced with another module 200. In this example, module 200 may be referred to as a disposable module.

In another embodiment, battery 210 is rechargeable, and module 200 further includes means for recharging battery 210 from an external electrical power source. In this example, module 200 may include an external electrical contact to receive electrical power (i.e., over wire) to recharge battery 208, and/or may include an inductive circuit to receive re-charge power inductively (i.e., wirelessly).

In FIG. 1, a module 106 may include a housing to contain electrical and/or mechanical components. The housing may be hermetically and/or permanently sealed.

A module 106 may be self-contained or self-sufficient in a hardware sense, in that the module 106 may be configured to operate without external physical electrical connectors.

A module 106 may be configured to operate independent of another module 106 (i.e., without interaction or coordination with the other module).

A module 106 may be configured to interact and/or coordinate with one another module 106. For example, a first one of modules 106 may be configured to communicate data to a second one of modules 106. The second module may be configured to communicate the data to an external device on behalf of the first module, and/or may be configured to process the data in combination, alone and/or in combination with other data.

In an embodiment, multiple modules 106 are functionally similar or identical to one another (e.g., identical circuitry with software/firmware-based configurability). In this example, a module and may be individually configurable, such as through I/O system 208 in FIG. 2, such as to perform one or more selectable and/or configurable functions.

In an embodiment, a module 106 includes circuitry and/or devices that differ from circuitry and/or devices of another module 106. For example, the first module in the example above may include a sensor and an I/O system to communicate with the second module, and the second module may include an I/O system to communicate with the first module and with an external device. In this example, the second module may be manufactured without a sensor.

A wearable modular device, such as described with reference to device 100 in FIG. 1, may be configured to attach to a wearable accessory such as, without limitation jewelry (e.g., necklace/pendant, finger ring, earring, body piercing, brooch, wrist bracelet, and/or wristwatch), a money clip, a belt buckle, a handbag, and/or an article of clothing. A wearable modular device, as described herein, may be configured as a clasp for a wearable accessory, and may be configured to replace an existing clasp (e.g., to replace a manufacturer's clasp), of the wearable accessory.

A wearable modular device, such as described with reference to device 100 in FIG. 1, may be configurable to attach to each of multiple variations of a wearable accessory (e.g., multiple types of wristwatches), and may be configurable to attach to each of multiple types of wearable accessories.

Examples are provided below with respect to wristwatches.

Figure 3:
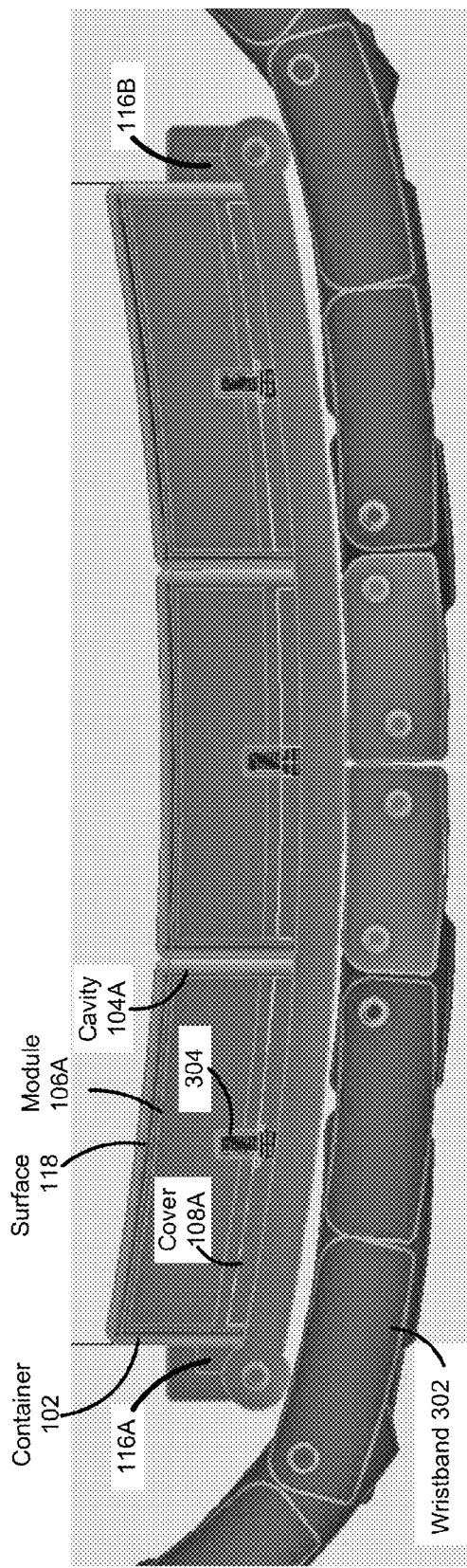
FIG. 3 is a cross-sectional side-view of a wearable modular device mounted to a wristwatch band.

FIG. 3 is a cross-sectional side-view of device 100 positioned within a wristwatch band 302. In this example, surface 118 of container 102 has a concave contour corresponding to a convex contour of a human wrist. This may help to maintain surface 118 in physical contact with a surface (e.g., skin) the wearer. Where a module 106 includes a biometric sensor, the concave contour of surface 118 may help to maintain the biometric sensor in relative close and/or sufficient proximity to the wearer.

In FIG. 3, covers 108 are secured over cavity 104 with screws 304.

A wristwatch may include a clasp to releasably secure a wristband around a wrist of a wearer. A wristwatch clasp may be configured as, without limitation, a hidden clasp (e.g., a butterfly clasp), a flip clasp, a security clasp, a buckle, and/or a metal band clasp.

Device 100 may be configured to mount to an existing wristband and/or to an existing clasp of a wristwatch (i.e., to a wristband and/or clasp provided by a manufacturer of the wristwatch).

In an embodiment, a replacement clasp or a replacement portion of a clasp (collectively referred to herein as a replacement clasp), is provided to replace an existing clasp or a portion thereof. The replacement clasp (or replacement portion), and device 100 may be configured to attach to one another, and may be configured to removably attach to one another.

A replacement clasp may be configured to connect to a strap-type wristband (e.g., leather, fabric, or synthetic), or to a metal wristband (e.g., solid and/or folded metal links), and/or may be configured to replace a particular type of existing clasp.

Alternatively, a replacement clasp may be configurable to connect to strap-type wristbands and metal wristbands, and/or may be configurable to replace multiple types of existing clasps. For example, an existing clasp and/or a wristband may include a removable pin or link to disconnect the existing clasp and wristband from one another. In this example, a replacement clasp may include a removable pin, a spring-loaded removable pin, a removable screw, a replacement link, and/or other mechanism(s) to couple the replacement clasp to the wristwatch band.

Figure 4:
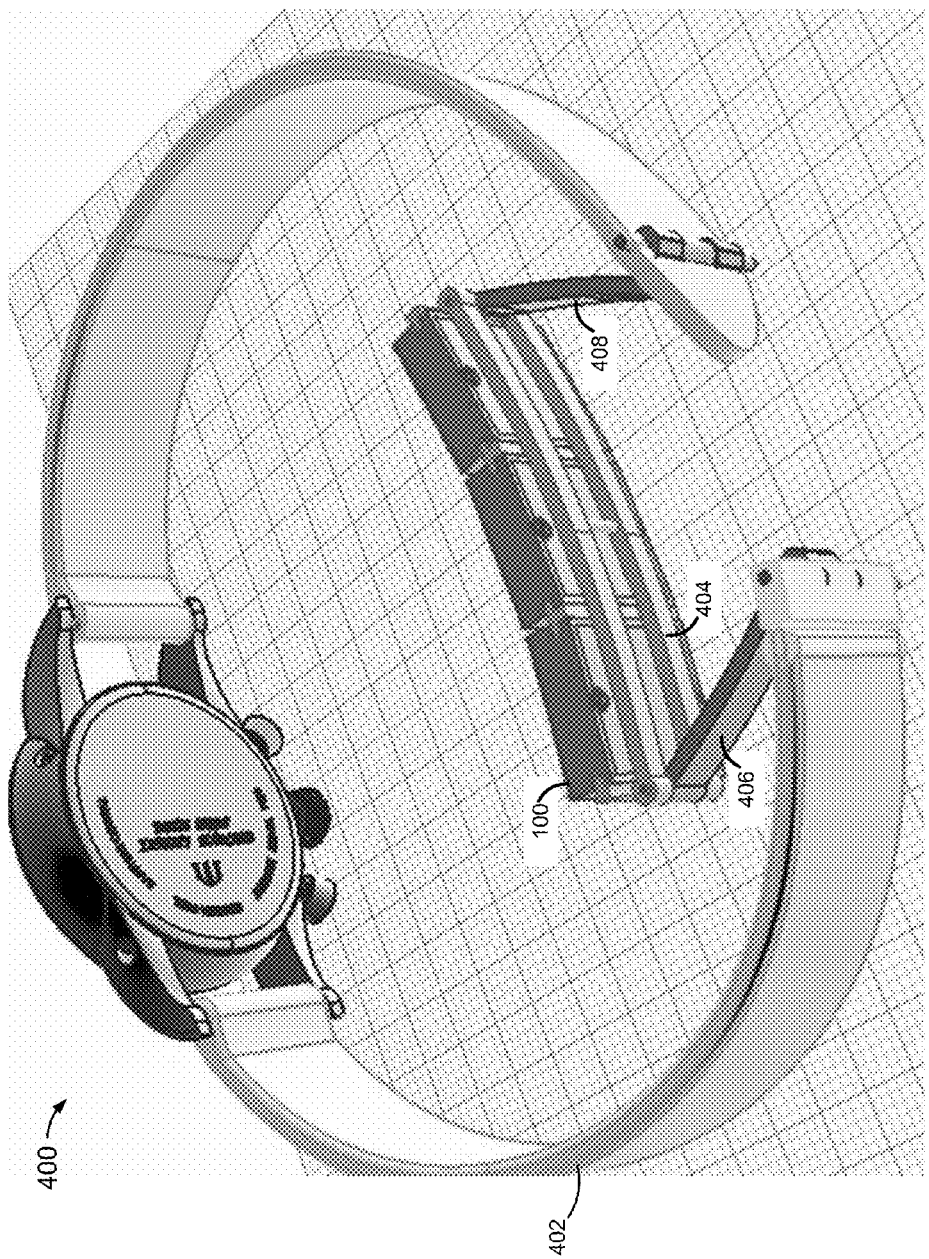
FIG. 4 is a perspective illustration of a wristwatch that includes a strap-type wristband, with a wearable modular device mounted to a replacement clasp.

FIG. 4 is a perspective illustration of a wristwatch 400 that includes a strap-type wristband 402, and device 100 mounted to clasp, illustrated here as a butterfly-type clasp.

In an embodiment, a butterfly clasp includes a bar and two arms, each arm having a first end hingedly coupled to a respective end of the bar, and a second end hingedly coupled to respective straps of a wristband, where the arms are movable between a first "collapsed" position (e.g., FIG. 106), in which second ends of the arms are drawn toward one another and pressed toward the bar to pull the straps toward one another to secure the wristband on the wrist of the wearer, and a second "expanded" position, in which the second ends of the arms are drawn away from the bar and away from one another to extend a length of the wristband to permit a wearer to slide a hand through the wristband.

In FIG. 4, the clasp includes a bar 404 and first and second arms 406 and 408, respectively. A first end of each arm 406 and 408 is hingedly connected to a respective end of bar 404. A second end of each arm 406 and 408 is hingedly connected to a respective end of wristband 402. The butterfly-type replacement clasp may be configured to replace an existing butterfly-type clasp and/or an existing non-butterfly-type clasp.

Bar 404 may be configured as described below with reference to one or more of FIGS. 23-28. Arms 406 and 408 may be configured as described below with reference to one or more of FIGS. 29-32.

Figure 5:
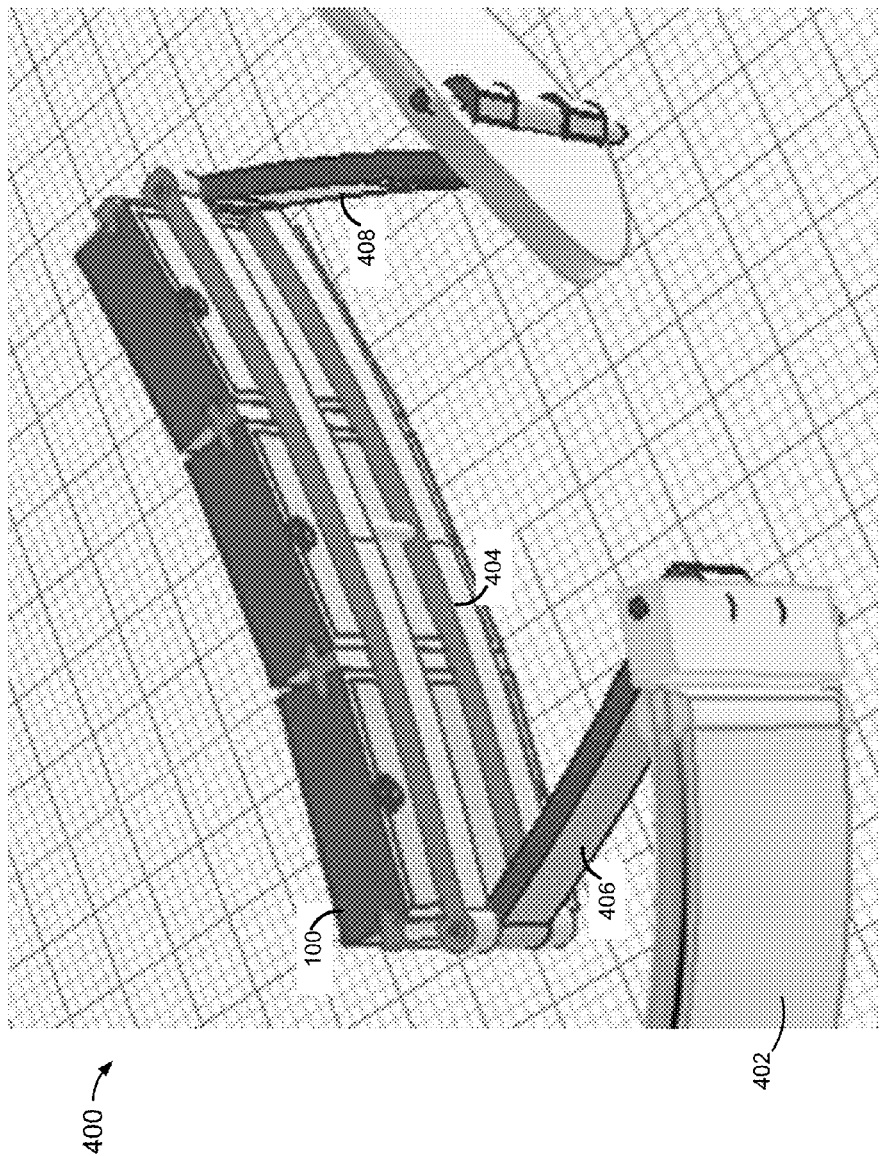
FIG. 5 is an expanded view of a portion of the wristwatch of FIG. 4.

FIG. 5 is an expanded view of a portion of wristwatch 400.

Figure 6:
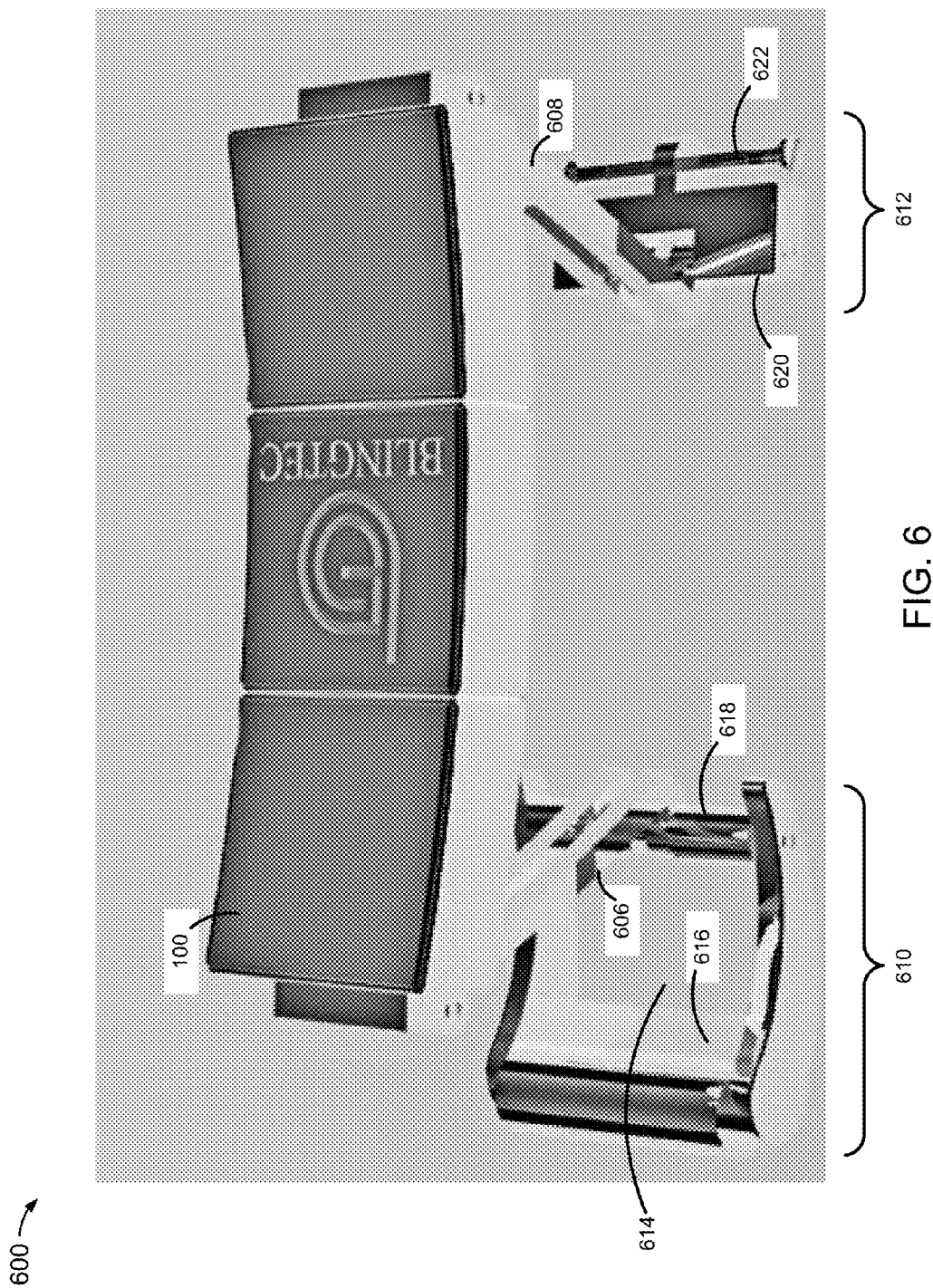
FIG. 6 is a perspective view of an assembly that includes a wearable modular device and a replacement butterfly-type clasp.

FIG. 6 is a perspective view of an assembly 600 that includes device 100 mounted to a butterfly-type clasp, which may represent a replacement butterfly-type clasp. The butterfly-type clasp includes first and second arms 606 and 608. A first end of each arm is hingedly connected to a bar, such as described above with reference to bar 404 in FIG. 4 and/or FIG. 5. A second end of arm 606 is connected to a first wristband connector 610, and a second end of arm 606 is connected to a second wristband connector 612.

First wristband connector 610 includes on opening 614 to receive a first end of a wrist strap, such as described further below with reference to FIG. 11. Connector 610 further includes a pinch portion 616 and hinge portion 618. Hinge portion or hinge pin 618. Pinch portion 616 is configured to pinch the first end of the wrist strap when assembly 600 is placed in a collapsed position, to secure to secure the wristband on the wrist of the wearer. Pinch portion 616 is further configured to release the first end of the wrist strap when assembly 600 is placed in an expanded position, to permit a wearer to slide a hand through the wristband.

In an embodiment, hinge portion 618 is fixedly coupled to pinch portion 616, and hingedly coupled to arm 606. In another embodiment, hinge portion 618 is fixedly coupled to arm 606, and pinch portion 616 is configured to rotate about hinge portion 618.

Figure 11:
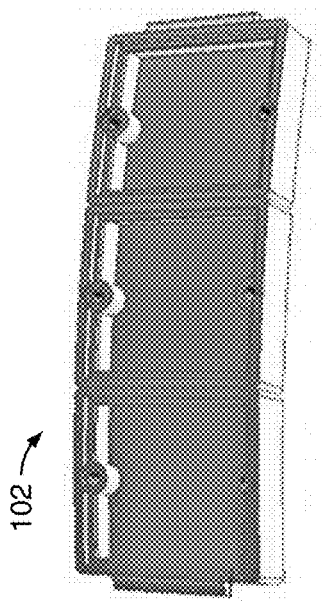
FIG. 11 is a perspective illustration of the container of FIG. 1.

Second wristband connector 612 includes a linkage portion or platform 620 that includes a pin 622 to couple to a second strap of a wristband, such as illustrated in FIG. 11. In this example, arm 608 is hingedly coupled to platform 620.

First and second wristband connectors 610 and 612 are configured to mount to respective ends of a wristband, and may be configurable, such as described further above.

Figure 7:
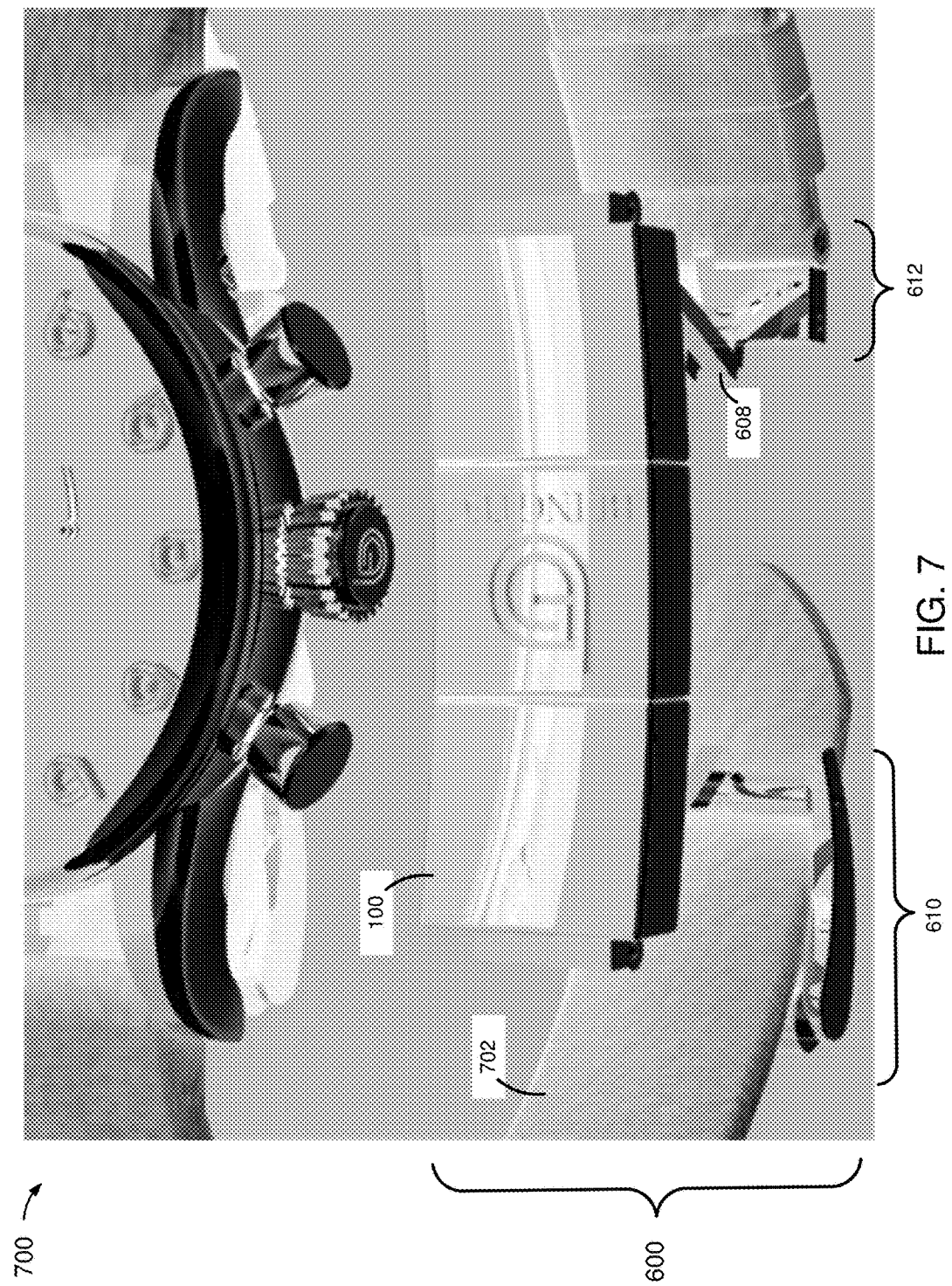
FIG. 7 is a perspective view of a wristwatch that includes the assembly of FIG. 6 mounted to a strap-type wristband.

FIG. 7 is a perspective view of a watch 700 that includes assembly 600 of FIG. 6 to attach container 100 to a strap-type wristband. In this example, wristband connector 610 is configured to receive a first strap 702 of the wristband through opening 614 (FIG. 6) of connector 610.

Figure 8:
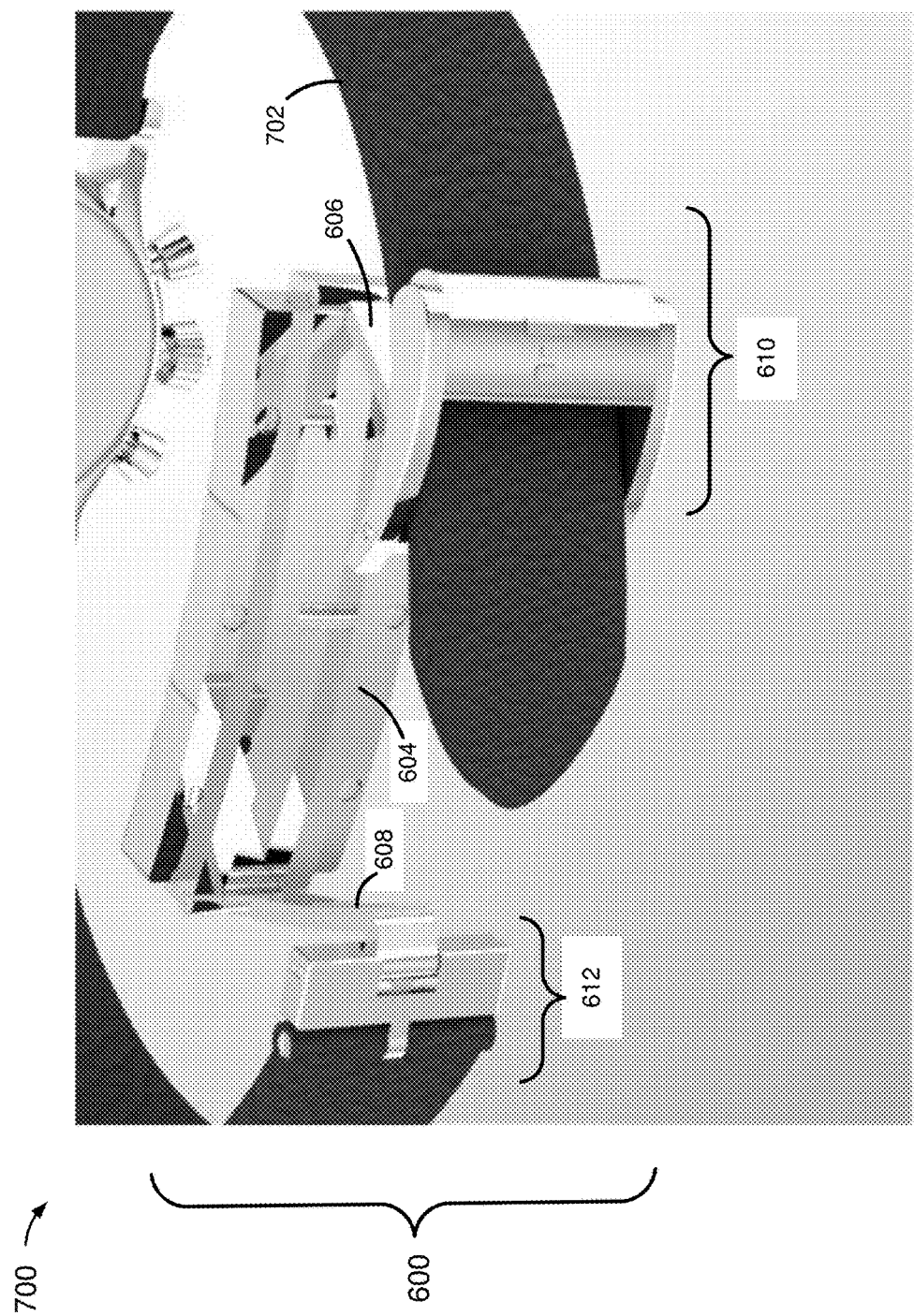
FIG. 8 is another perspective view of the wristwatch of FIG. 9.
Figure 9:
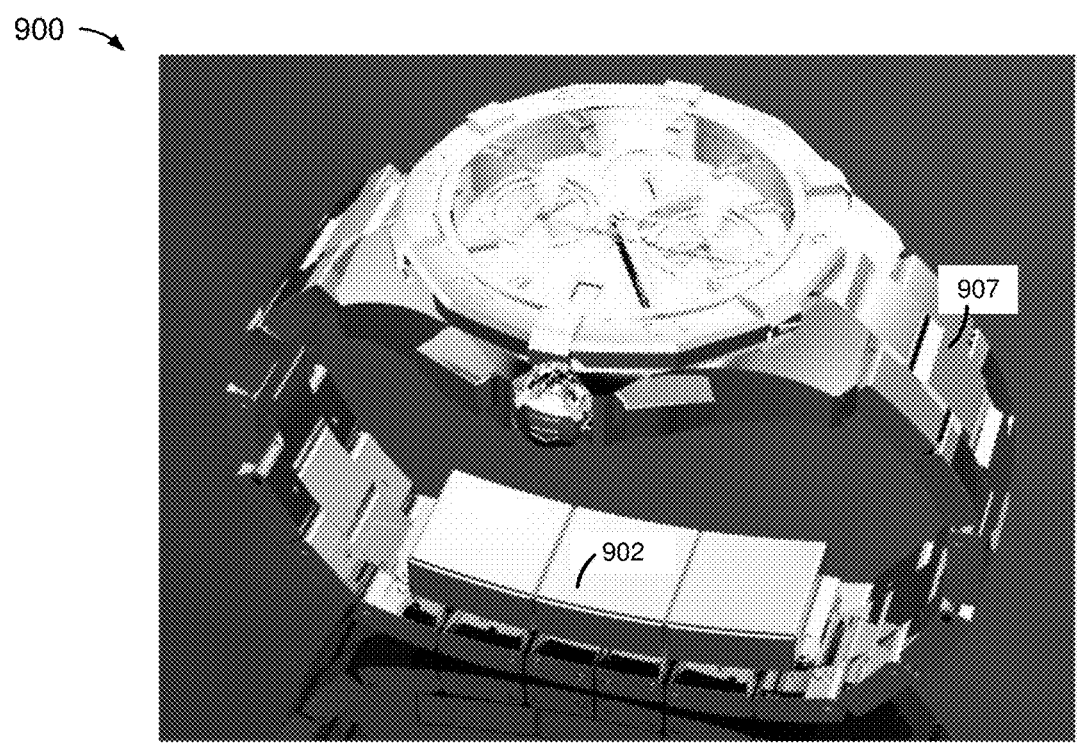
FIG. 9 is a perspective view of another wristwatch that includes the assembly of FIG. 6 mounted to a metal wristband.

FIG. 8 is another perspective view of watch 700.9 FIG. 9 is a perspective view of a watch 900, that includes assembly 600 mounted to a metal wristband 902.

In an embodiment, assembly 600 is configured to attach to a strap-type wristband, such as illustrated in one or more of FIGS. 7 and 8, and one or more components of first and/or second wristband connectors 610 and 612 are removable to permit connection of a remaining portion of assembly 600 to a metal watchband.

Figure 10:
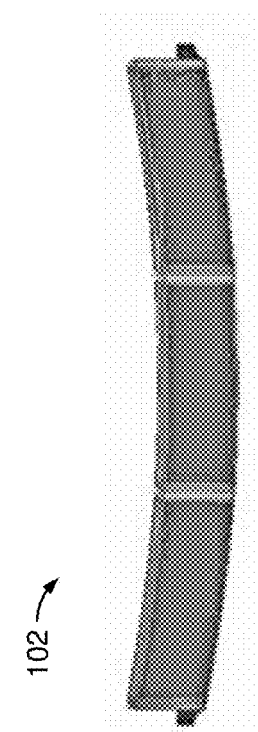
FIG. 10 is a side-view illustration of the container of FIG. 1.

FIG. 10 is a side-view illustration of container 102.

FIG. 11 is a perspective illustration of container 102.

Figure 12:
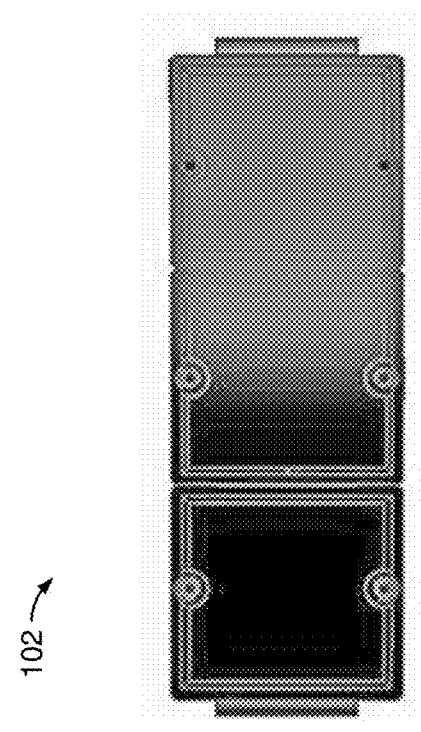
FIG. 12 is another perspective illustration of the container of FIG. 1.

FIG. 12 is another perspective illustration of container 102.

Figure 13:
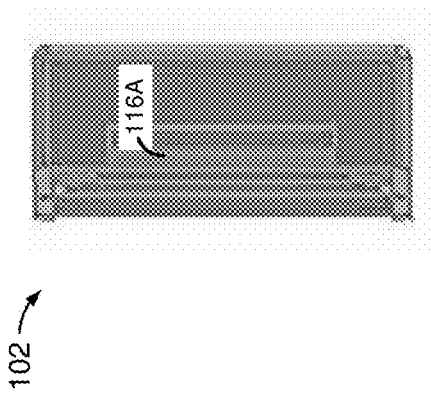
FIG. 13 is an end-view illustration of the container of FIG. 1.

FIG. 13 is an end-view illustration of container 102.

FIG. 14 is a side-view illustration of covers 108.

FIG. 15 is a perspective illustration of covers 108.

Figure 16:
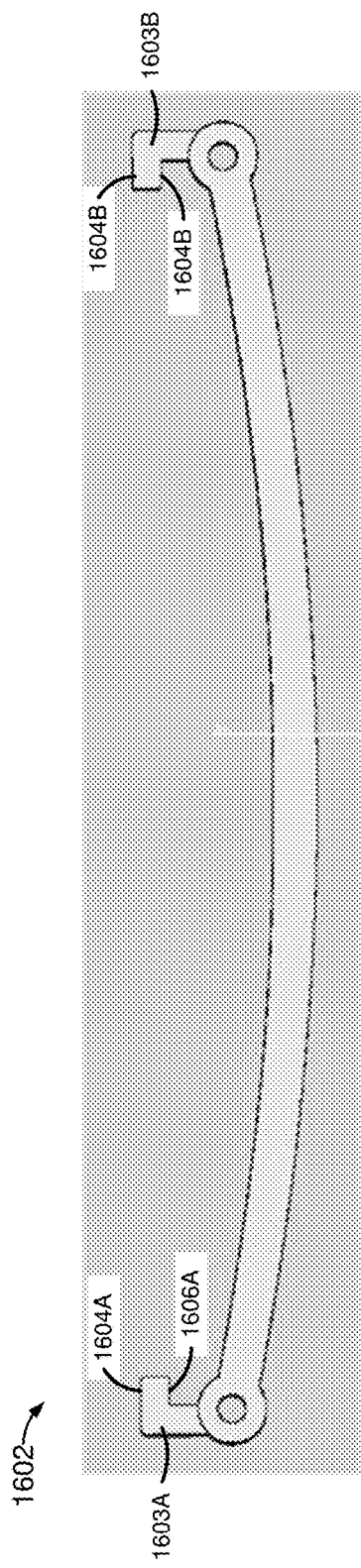
FIG. 16 is a side-view illustration of a bar, such as illustrated in FIG. 4.

FIG. 16 is a side-view illustration of a bar 1602, which may represent an example embodiment of bar 404 in FIG. 4. In FIG. 16, bar 1602 includes protrusions 1603, each including an extension portion 1604 to provide a captive region 1606 to receive a corresponding one of protrusions 116 of container 102 (FIG. 1).

With reference to the orientation of container 102 illustrated in FIG. 10, and the orientation of bar 1602 illustrated in FIG. 16, protrusions 116 of container 102 (FIG. 1), may be configured to slideably engage/disengage captive regions 1606 when container 102 is moved towards or away from bar 404 (e.g., into or out of the plane of FIG. 16).

Figure 17:
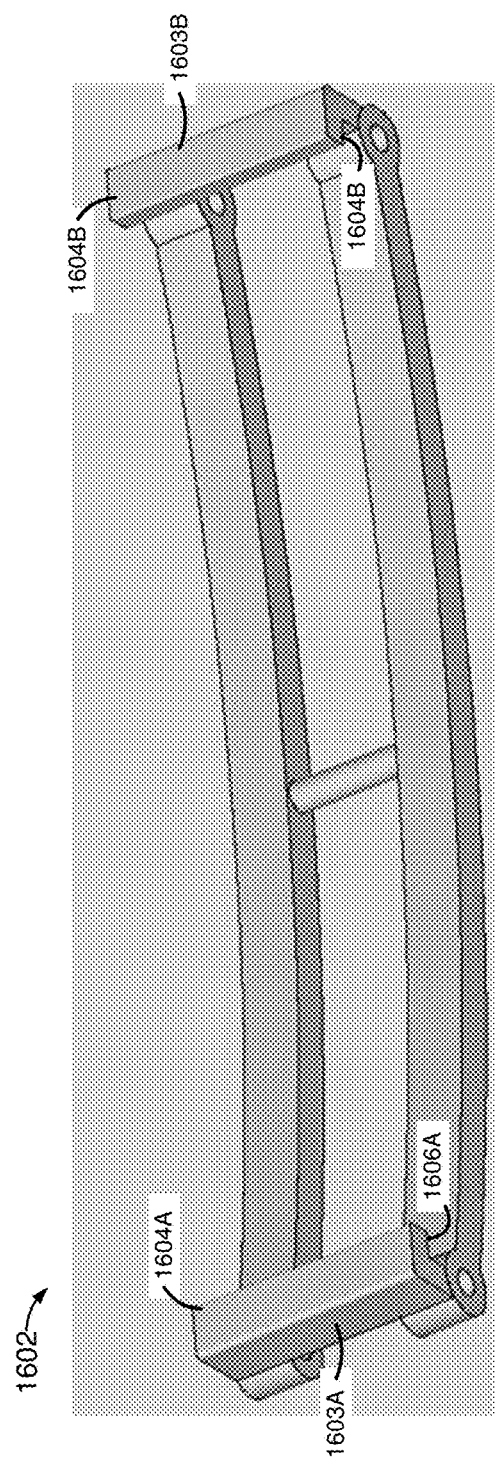
FIG. 17 is a perspective illustration of the bar of FIG. 19.

FIG. 17 is a perspective illustration of bar 1602.

FIG. 18 is a side-view illustration of arms 1802 and 1804, which may represent example embodiments of arms 406 and 408, respectively, in FIG. 4.

FIG. 19 is a perspective illustration of arms 1802 and 1804.

FIG. 20 is a perspective illustration of one of arms 1802 and 1804.

FIG. 21 is another perspective illustration of one of arms 1802 and 1804.

Figure 22:
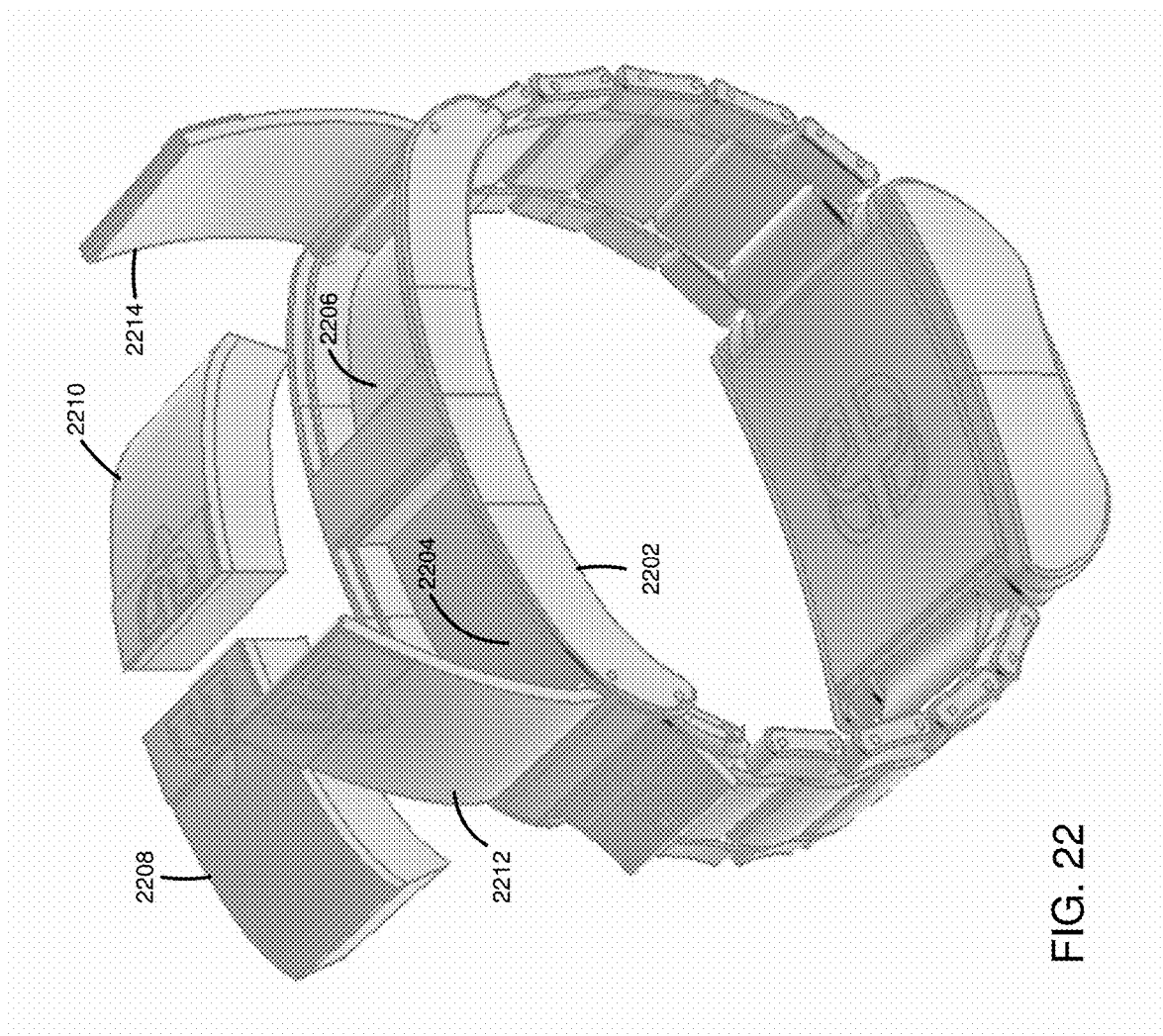
FIG. 22 is an illustration of wristwatch apparatus that includes a butterfly-type clasp and integral container assembly (clasp assembly).

FIG. 22 is an illustration of wristwatch apparatus 2200 that includes a butterfly-type clasp and integral container assembly (clasp assembly) 2202. Clasp assembly 2202 has first and second cavities 2204 and 2206 to receive respective electronics modules 2208 and 2210. Clasp assembly 2202 further includes hinged covers 2212 and 2214 to enclose respective cavities 2204 and 2206. In this example, hinged covers 2212 and 2214 are configured to open outwardly, away from a wrist of a wearer. This may be useful to permit the wearer to access cavities 2204 and 2206 (e.g., to access or replace electronics modules 2208 and 2210), without having to remove the wristband.

Figure 23:
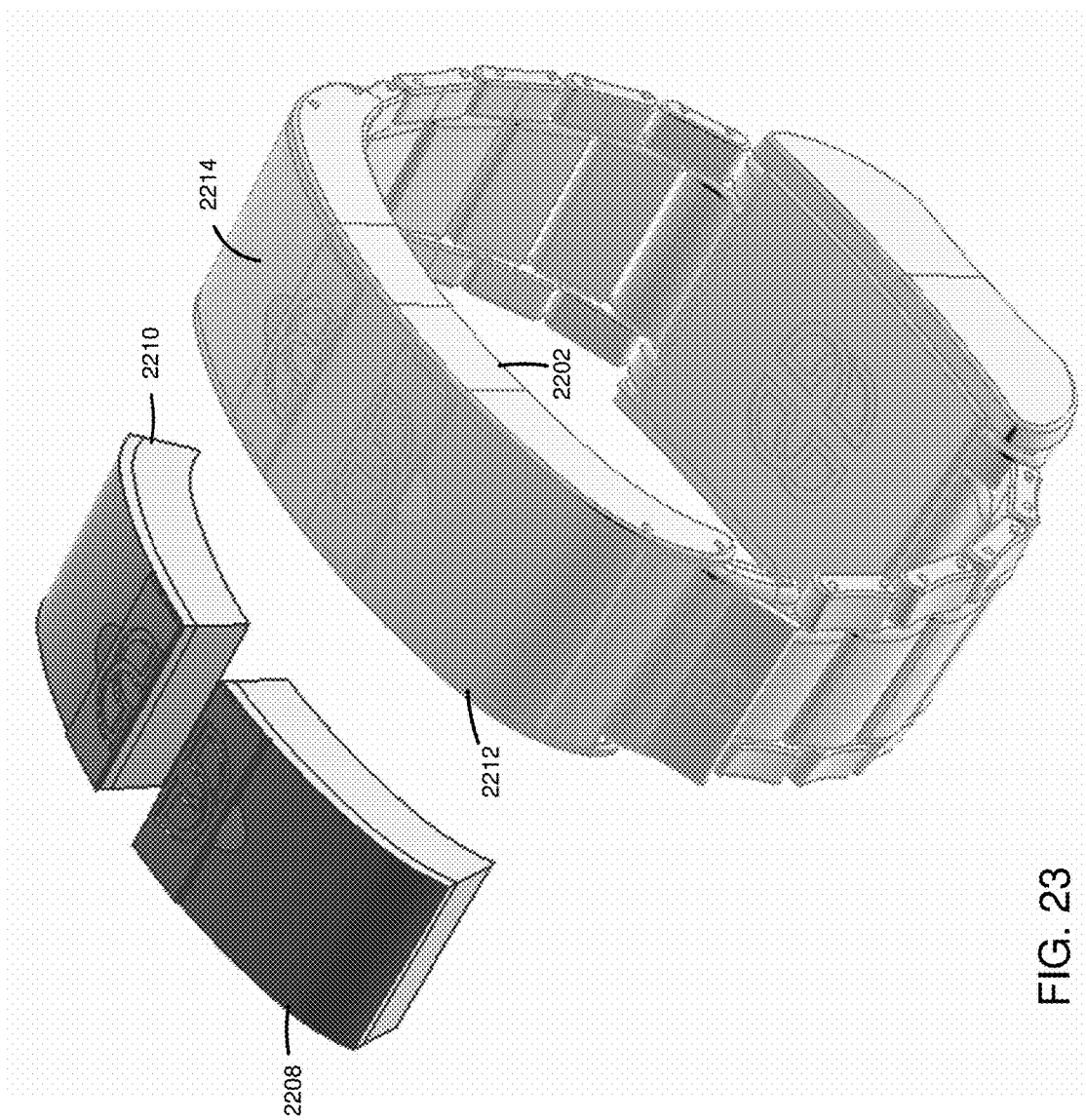
FIG. 23 is another illustration of the wristwatch apparatus of FIG. 25.

FIG. 23 is another illustration of wristwatch apparatus 2200.

Figure 24:
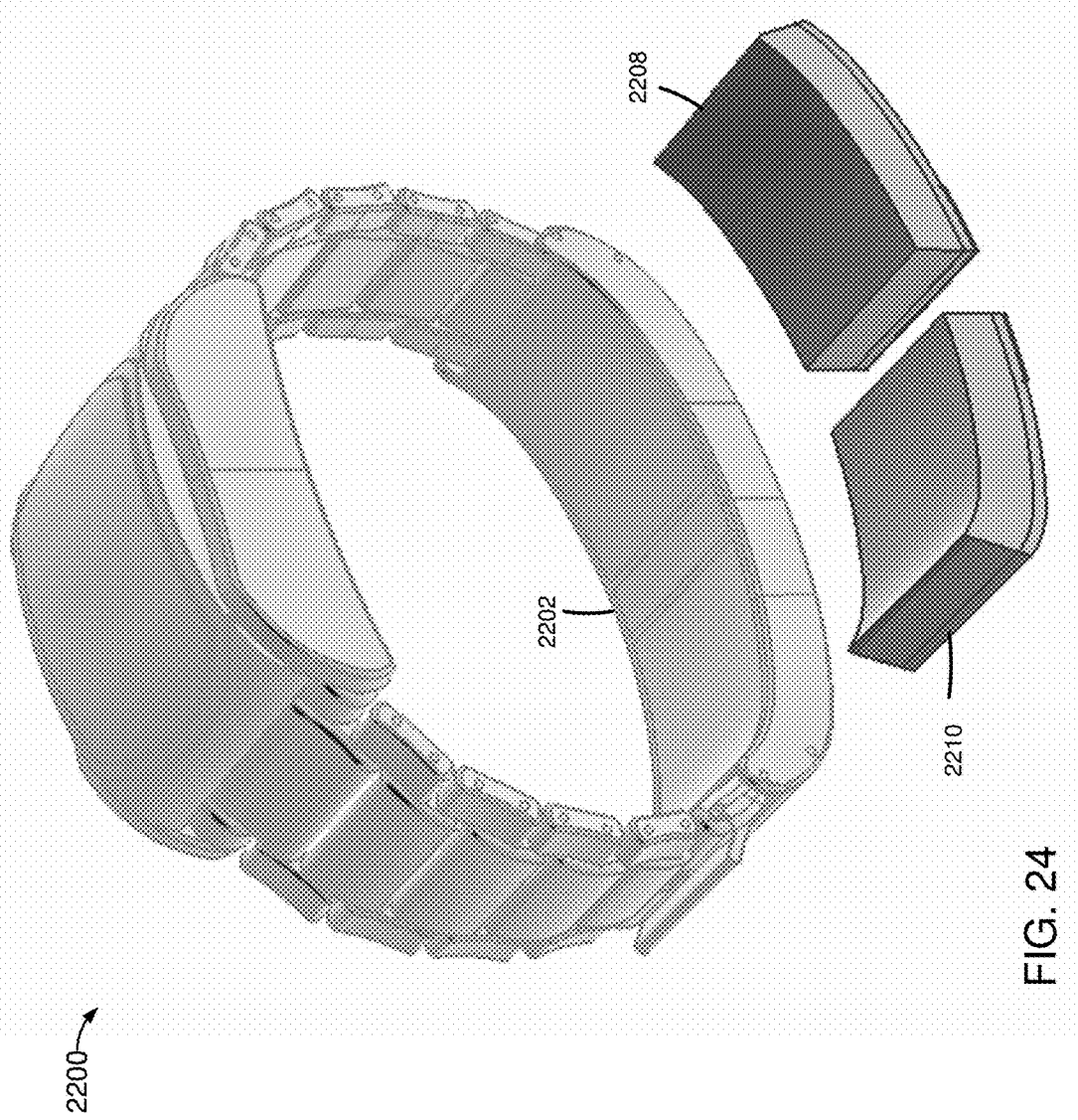
FIG. 24 is another illustration of the wristwatch apparatus of FIG. 25.

FIG. 24 is another illustration of wristwatch apparatus 2200.

Figure 25B:
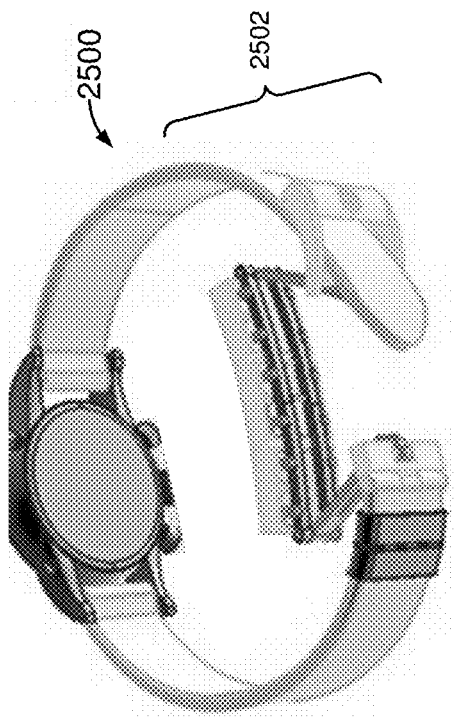
FIG. 25B is another illustration of the wristwatch apparatus of FIG. 28A.
Figure 25D:
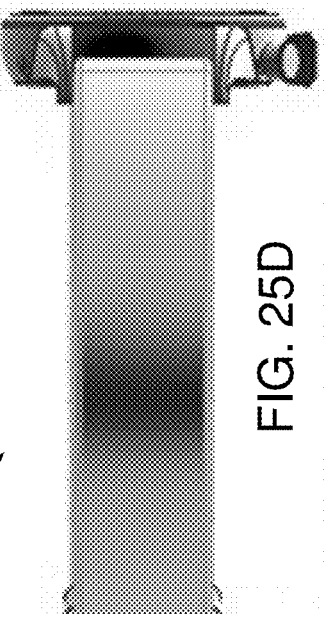
FIG. 25D is another illustration of the wristwatch apparatus of FIG. 28A.
Figure 25A:
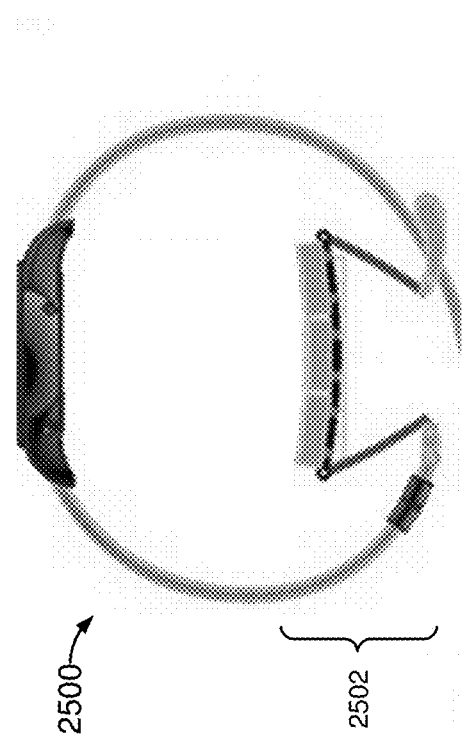
FIG. 25A is an illustration of another wristwatch apparatus that includes clasp assembly.

FIG. 25A is an illustration of a wristwatch apparatus 2500 that includes clasp assembly 2802.

FIG. 25B is another illustration of wristwatch apparatus 2500.

Figure 25C:
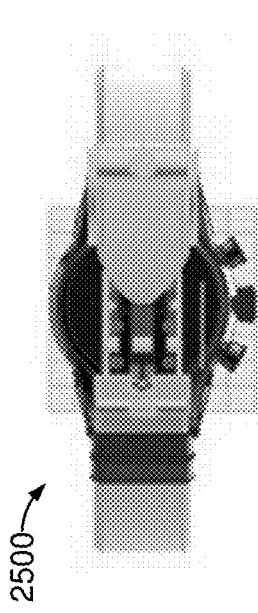
FIG. 25C is another illustration of the wristwatch apparatus of FIG. 28A.

FIG. 25C is another illustration of wristwatch apparatus 2500.

FIG. 25D is another illustration of wristwatch apparatus 2500.

Figure 26:
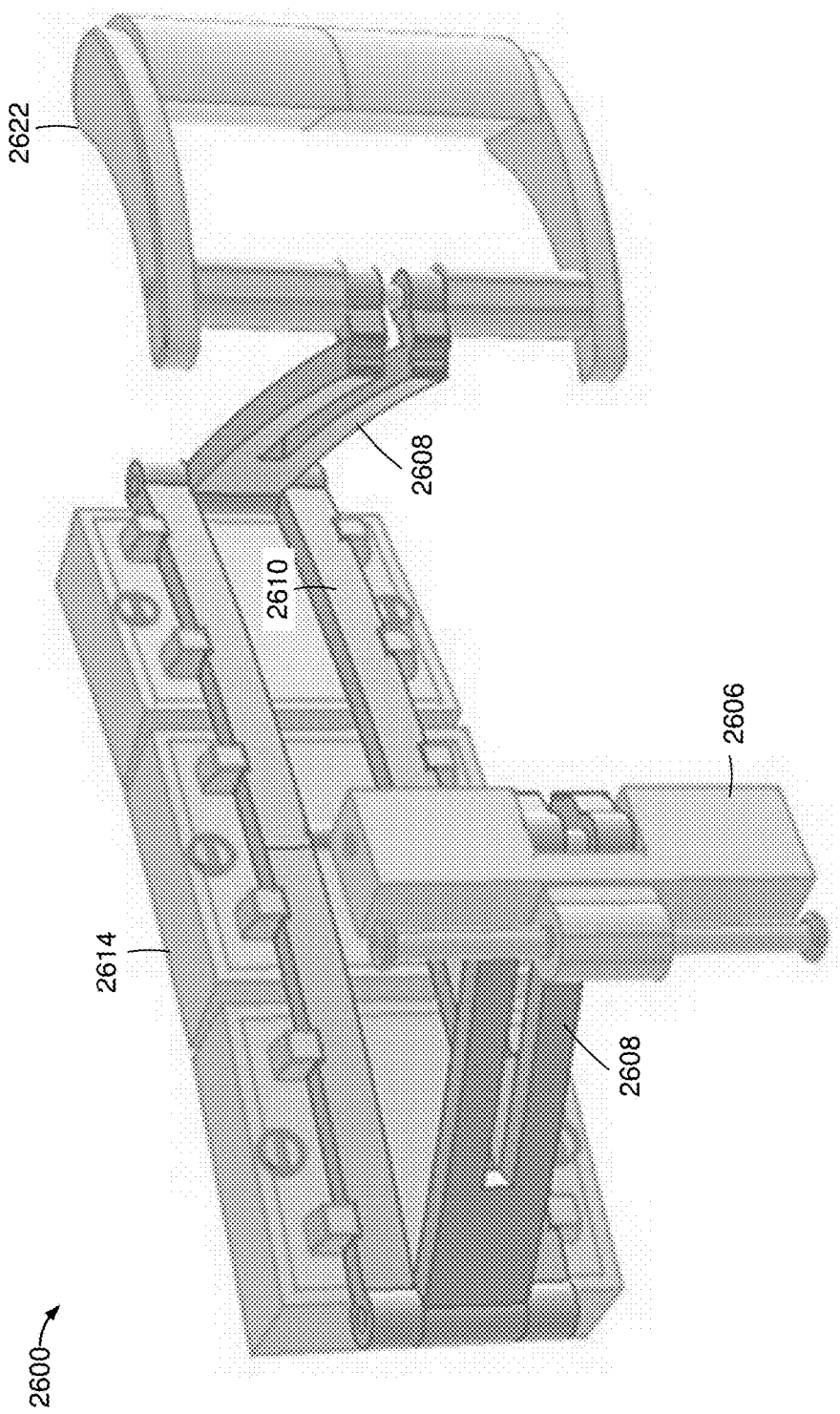
FIG. 26 is an illustration of a clasp assembly.

FIG. 26 is an illustration of clasp assembly 26000 that includes components 2602-2626.

Figure 27:
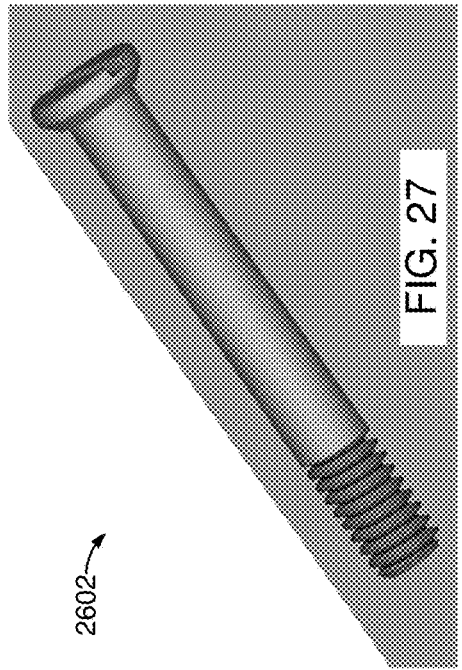

FIG. 27 is an illustration of a component 2602 of clasp assembly 2600.

Figure 28:
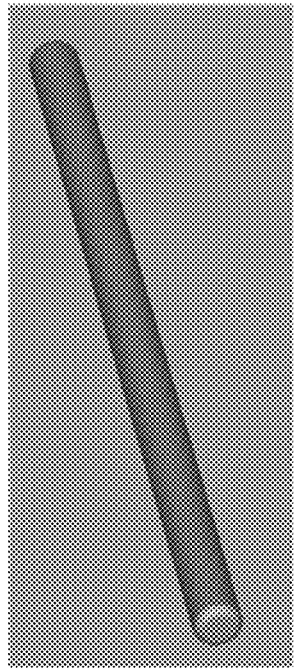
FIGS. 27 through 38 are illustrations of components of the clasp assembly of FIG. 26.

FIG. 28 is an illustration of a component 3104 of clasp assembly 2600.

Figure 29:
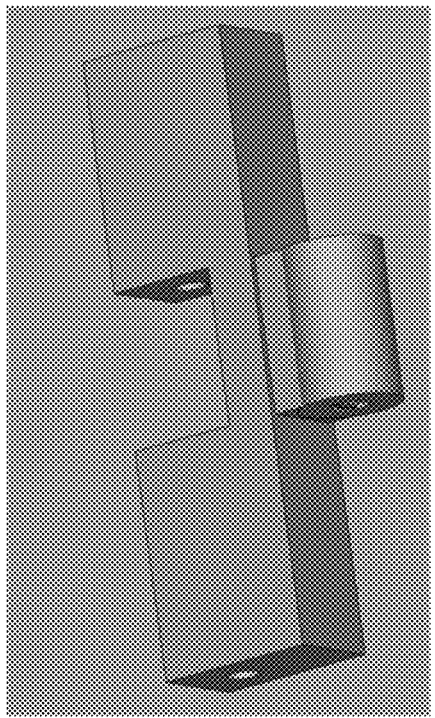

FIG. 29 is an illustration of a component 3106 of clasp assembly 2600.

Figure 30:
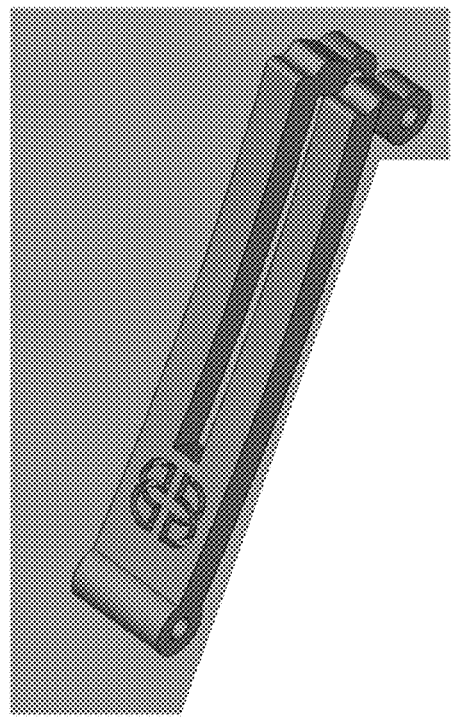

FIG. 30 is an illustration of a component 3108 of clasp assembly 2600.

Figure 31:
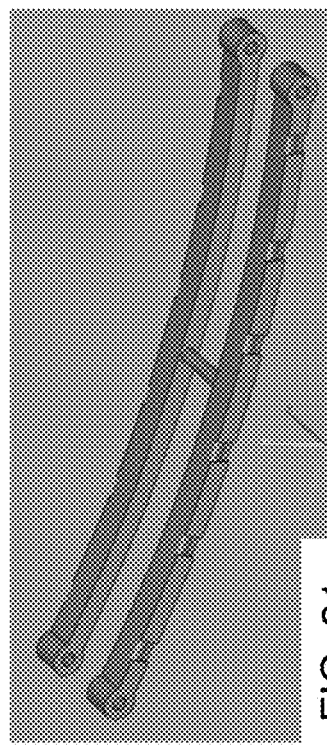

FIG. 31 is an illustration of a component 3110 of clasp assembly 2600.

Figure 32:
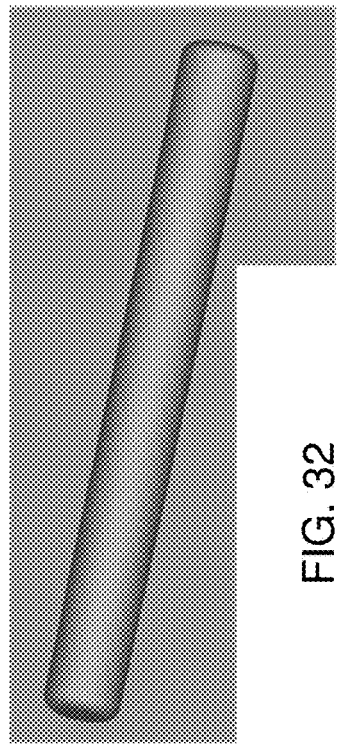

FIG. 32 is an illustration of a component 3112 of clasp assembly 2600.

Figure 33:
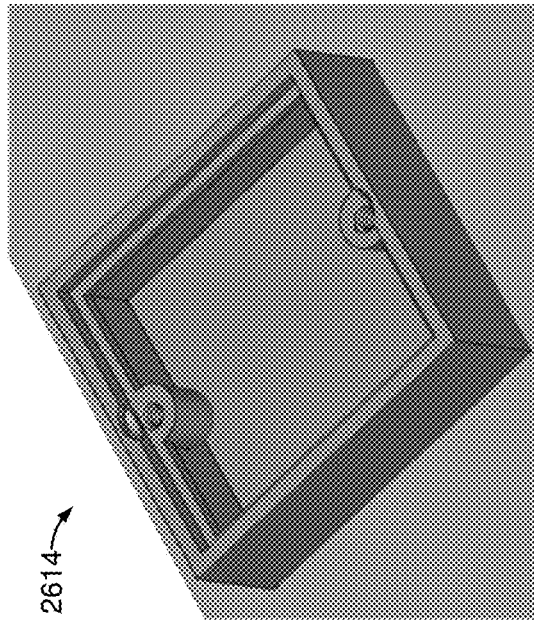

FIG. 33 is an illustration of a component 3114 of clasp assembly 2600.

Figure 34:
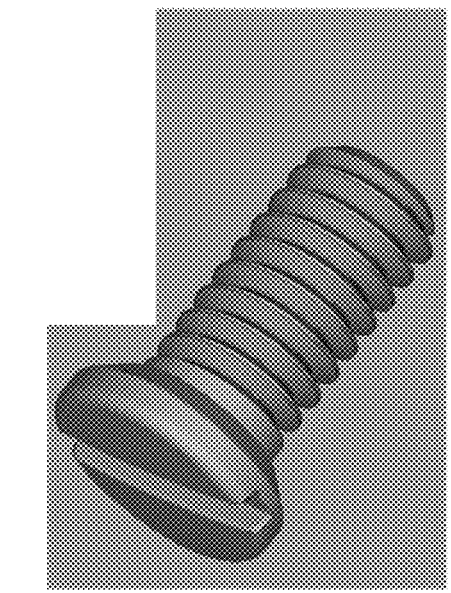

FIG. 34 is an illustration of a component 3116 of clasp assembly 2600.

Figure 35:
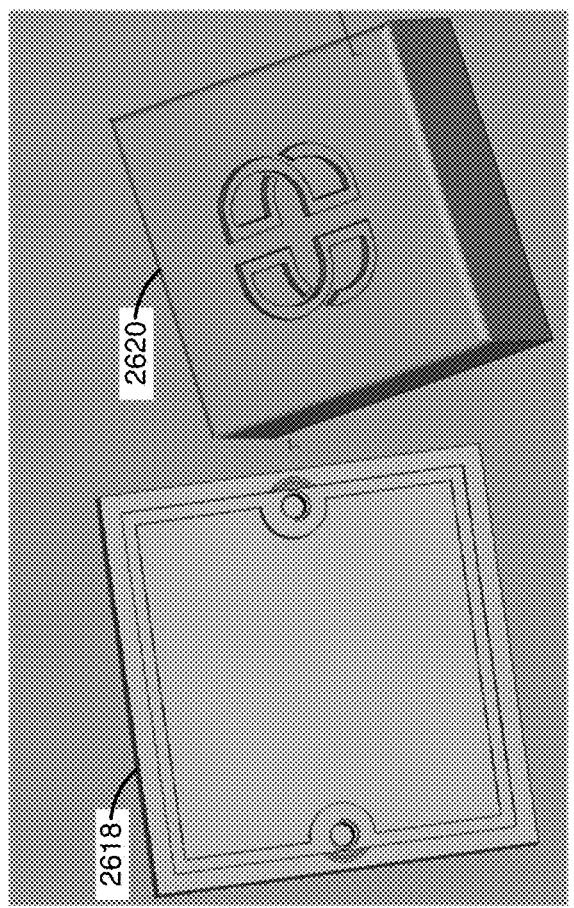

FIG. 35 is an illustration of components 3118 and 3120 of clasp assembly 2600.

Figure 36:
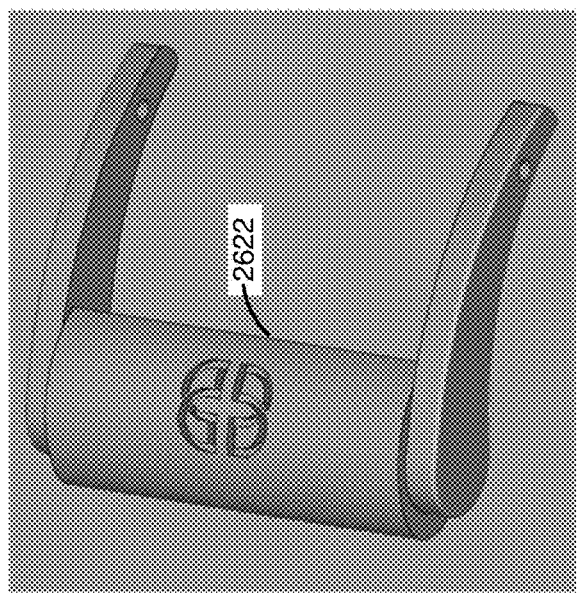

FIG. 36 is an illustration of a component 3322 of clasp assembly 2600.

Figure 37:
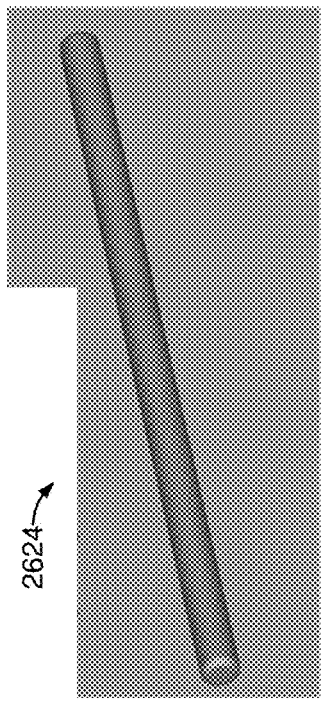

FIG. 37 is an illustration of a component 3324 of clasp assembly 2600.

Figure 38:
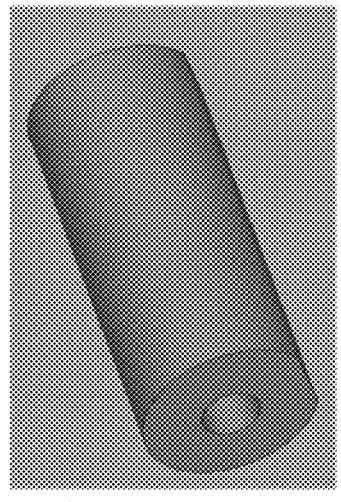

FIG. 38 is an illustration of a component 3326 of clasp assembly 2600.

Figure 39B:
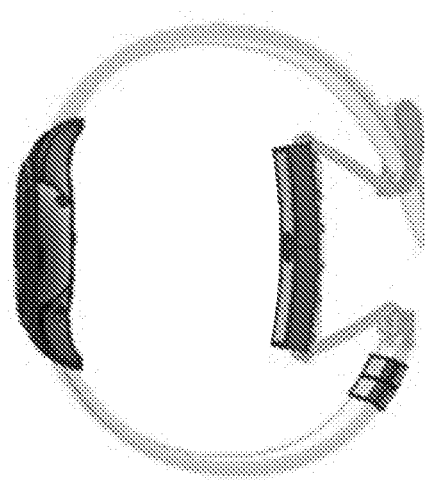
FIG. 39B is another illustration of the wristwatch apparatus of FIG. 39A.
Figure 39D:
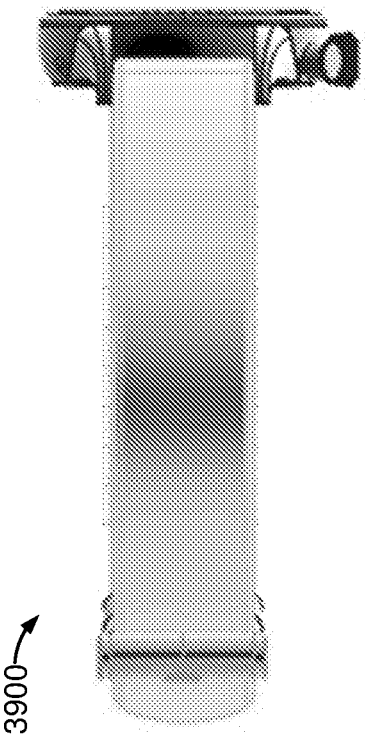
FIG. 39D is another illustration of the wristwatch apparatus of FIG. 39A.
Figure 39A:
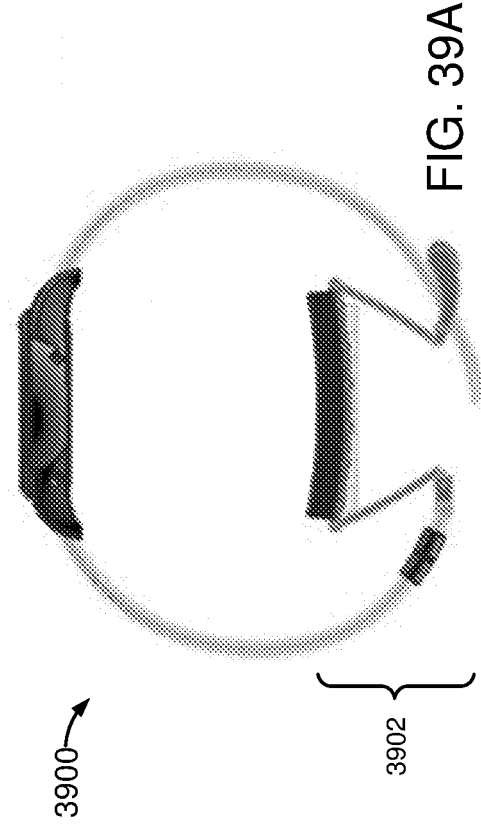
FIG. 39A is an illustration of another wristwatch apparatus that includes a clasp assembly.

FIG. 39A is an illustration of a wristwatch apparatus 3900 that includes a clasp assembly 3902.

FIG. 39B is another illustration of wristwatch apparatus 3900.

Figure 39C:
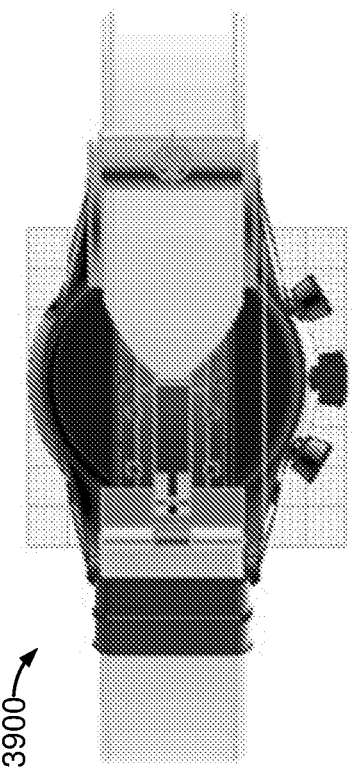
FIG. 39C is another illustration of the wristwatch apparatus of FIG. 39A.

FIG. 39C is another illustration of wristwatch apparatus 3900.

FIG. 39D is another illustration of wristwatch apparatus 3900.

Figure 40:
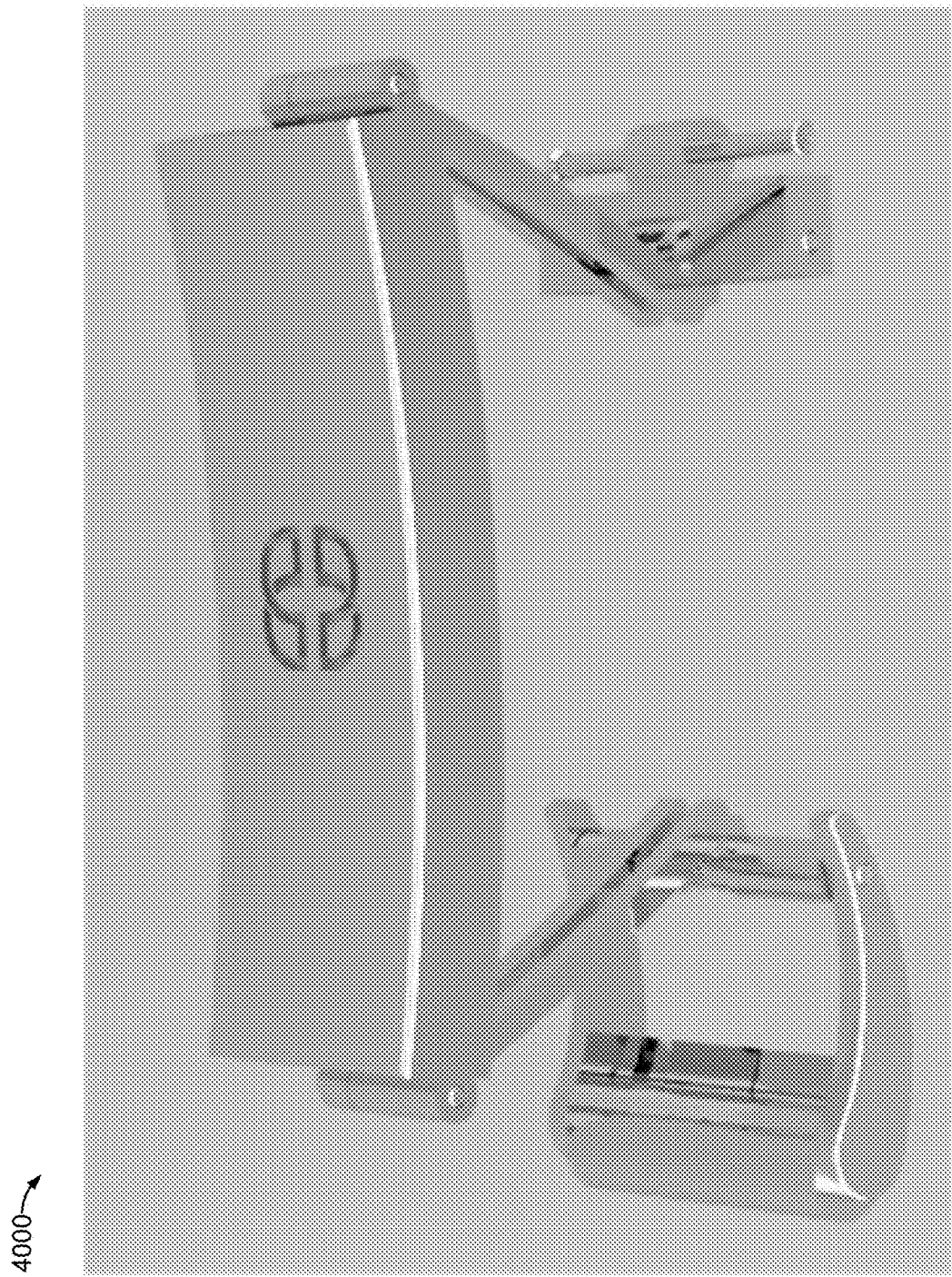
FIG. 40 is an illustration of another clasp assembly.

FIG. 40 is an illustration of a clasp assembly 4000, which may include components similar to clasp assembly 2600 in FIG. 26.

Figure 41:
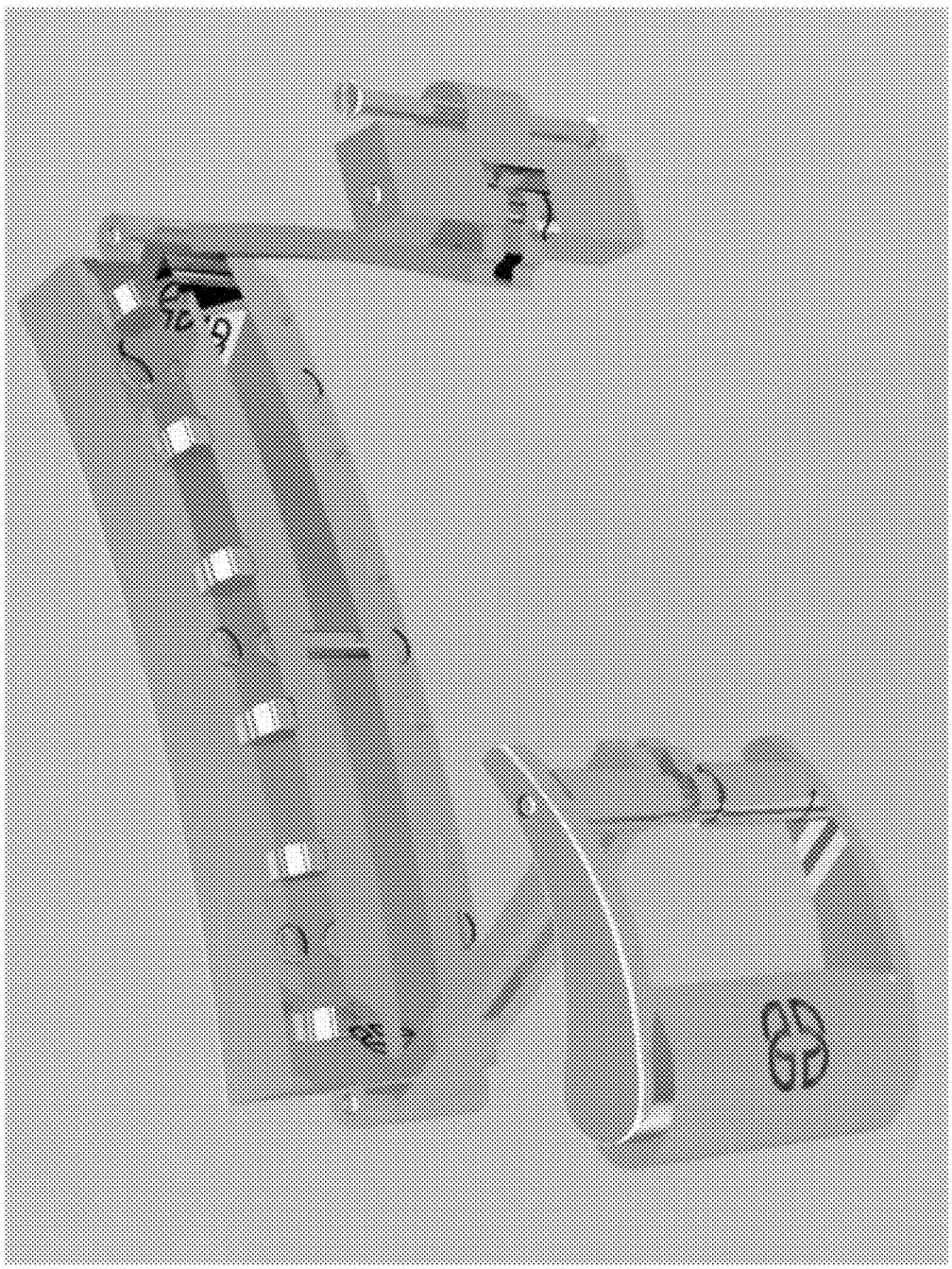
FIG. 41 is another illustration of a portion of the clasp assembly of FIG. 40.

FIG. 41 is another illustration of a portion of clasp assembly 4000.

Figure 42:
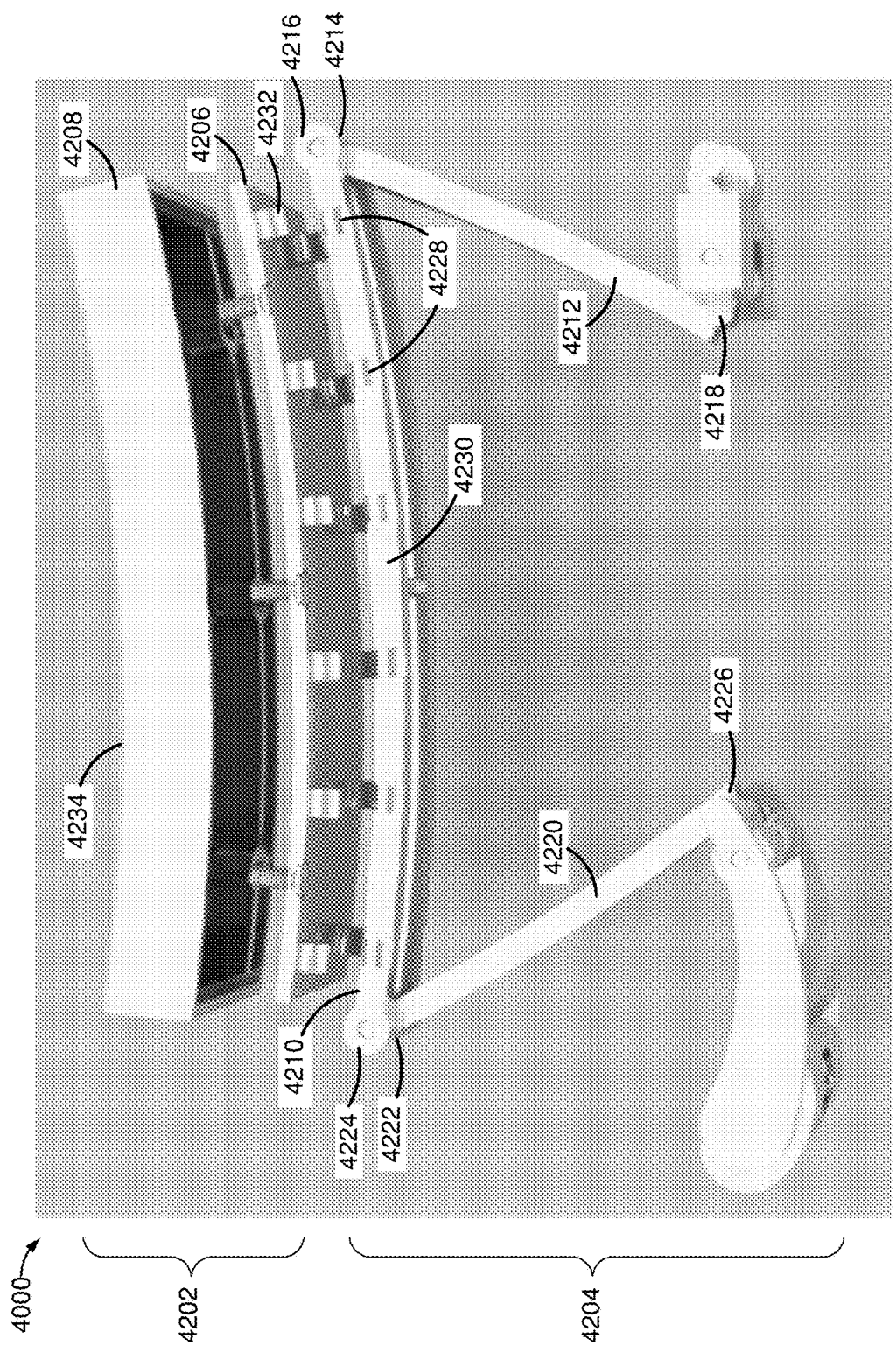
FIG. 42 is another illustration of a portion of the clasp assembly of FIG. 40.

FIG. 42 is another illustration of a portion of clasp assembly 4000. Clasp assembly 4000 includes a container 4202 and a butterfly-type connection device 4204. Container 4202 includes a base portion 4206 and a body portion 4208. Butterfly-type connection device 4204 includes a bar 4210. Butterfly-type connection device 4204 further includes a first arm 4212 having a first end 4214 hingedly coupled to a first end 4216 of bar 4210, and a second end 4218 configured to hingedly couple to a first strap of a wristband. Butterfly-type connection device 4204 further includes a second arm 4220 having a first end 4222 hingedly coupled to a second end 4224 of bar 4210, and second end 4226 configured to couple to a second strap of the wristband. In the example of FIG. 42, bar 4210 has multiple concave indents 4228 along a first edge 4230. Similar concave indents are provided along a second edge of bar 4210, which is opposite first edge 4230. Further in this example, container 4202 includes multiple tabs 4232 extending from base portion 4206, configured to engage respective ones of concave indents 4228 of bar 4210 to secure container 4202 and bar 4210 to one another. In the example of FIG. 42, butterfly-type connection device 4204 is configured to connect container 4202 to a wristband such that a surface 4234 of container 4202 is maintained in physical contact with a wearer of the wristband.

Figure 43:
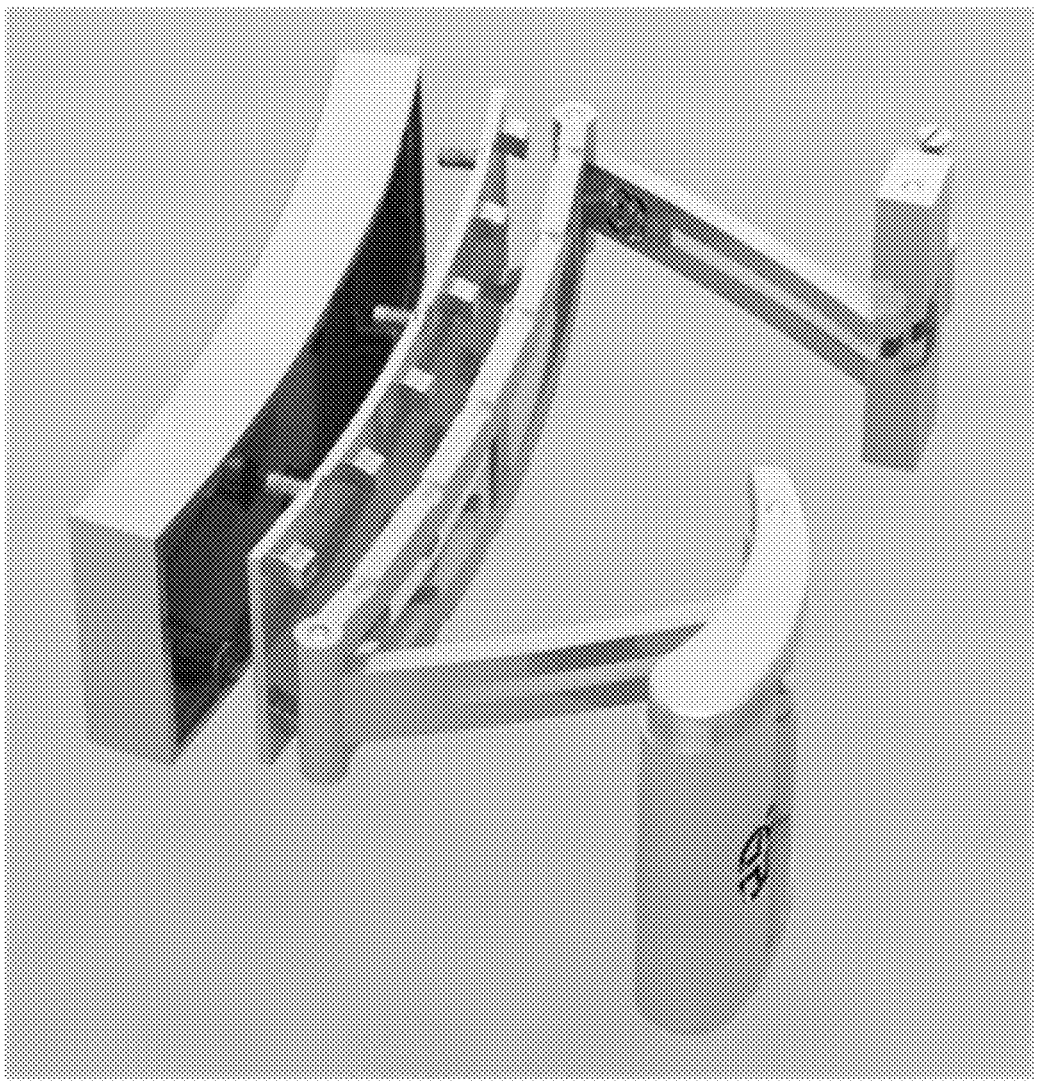
FIG. 43 is another illustration of a portion of the clasp assembly of FIG. 40.

FIG. 43 is another illustration of a portion of clasp assembly 4000.

Figure 44:
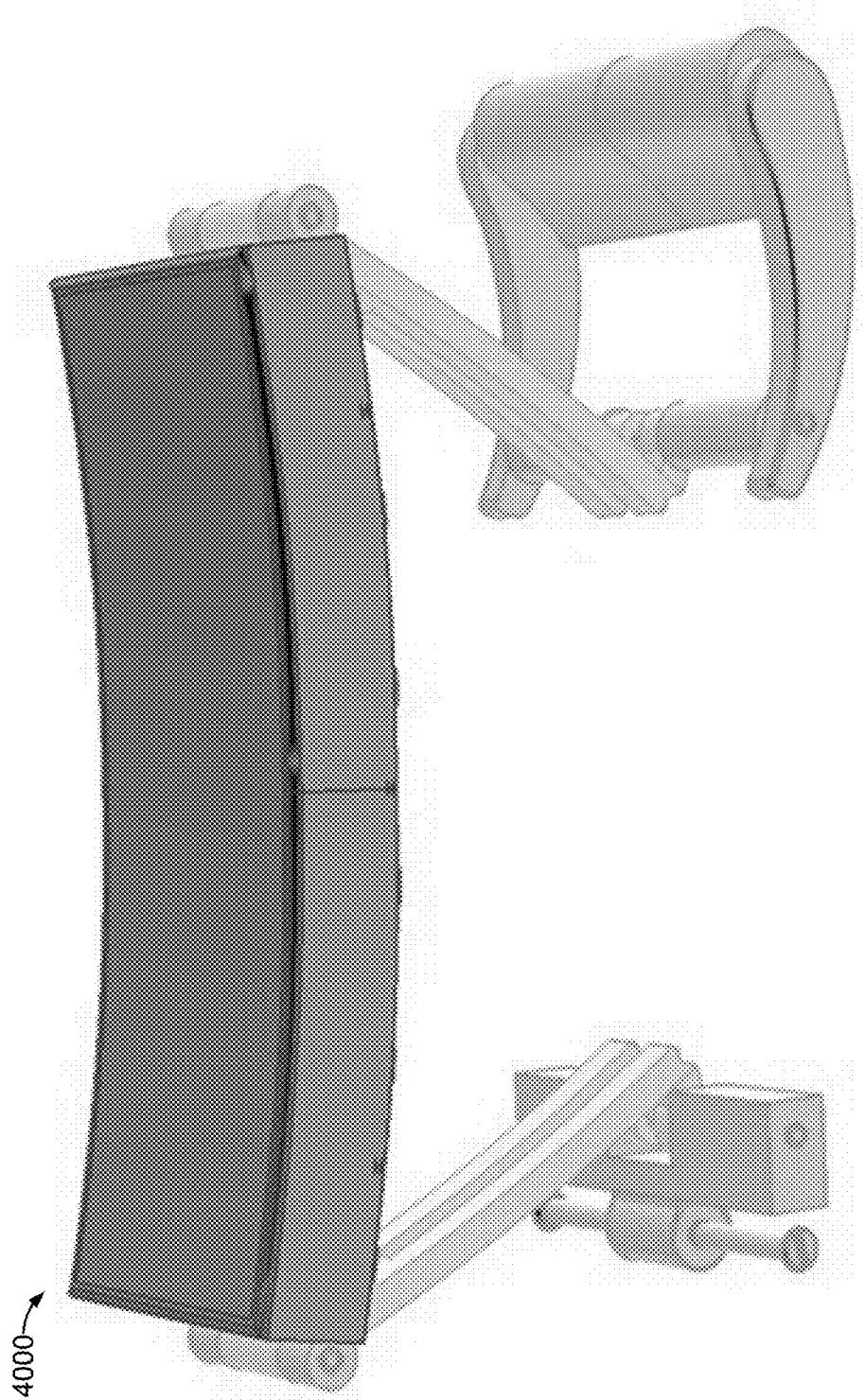
FIG. 44 is another illustration of a portion of the clasp assembly of FIG. 40.

FIG. 44 is another illustration of a portion of clasp assembly 4000.

Figure 45:
FIG. 45 is an illustration of another wristwatch apparatus that includes a clasp assembly.

FIG. 45 is an illustration of a wristwatch apparatus 4500 that includes a clasp assembly 4502.

Figure 46:
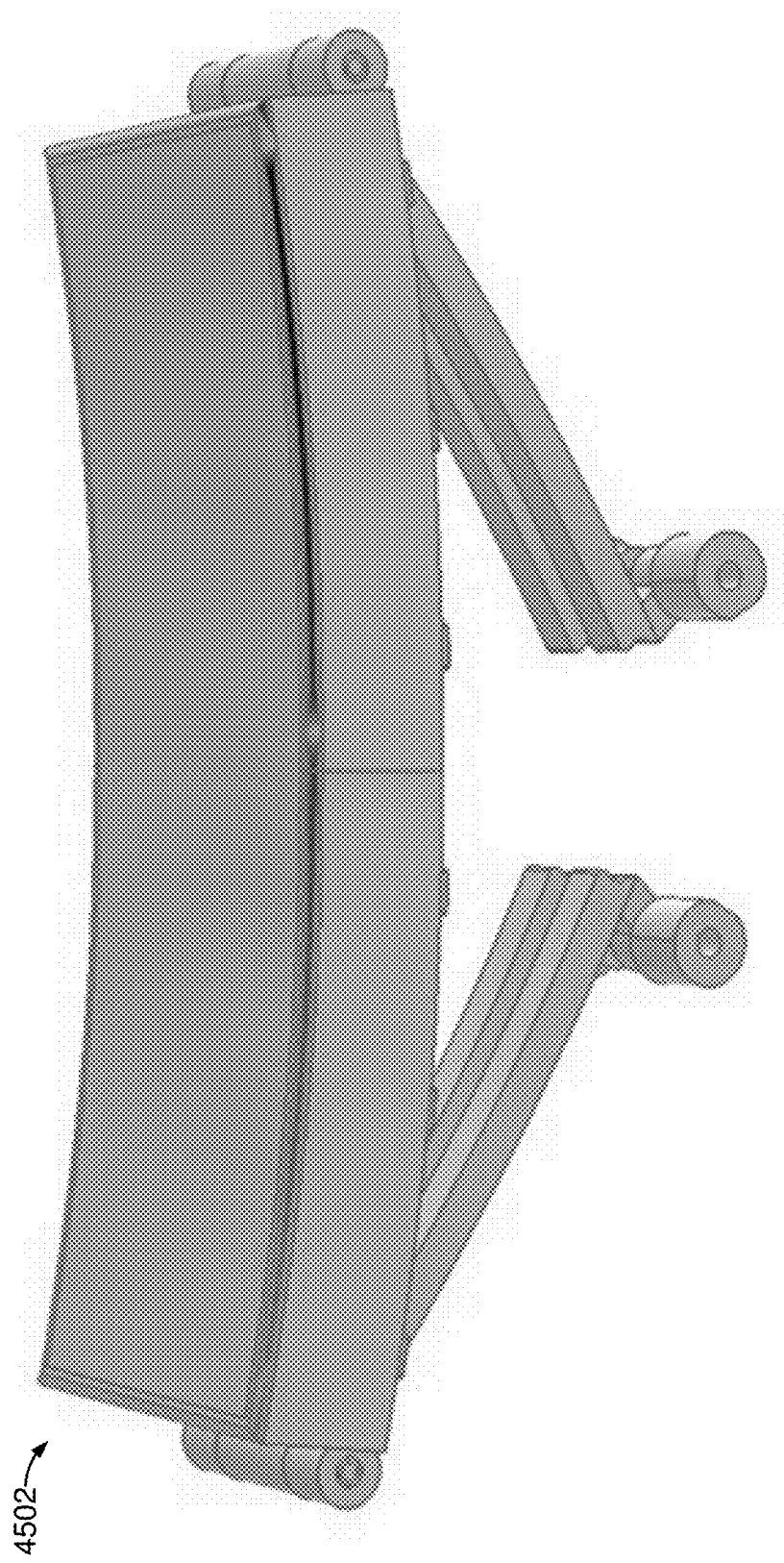
FIG. 46 is an illustration of a portion of the clasp assembly of FIG. 45.

FIG. 46 is an illustration of a portion of clasp assembly 4502.

Figure 47:
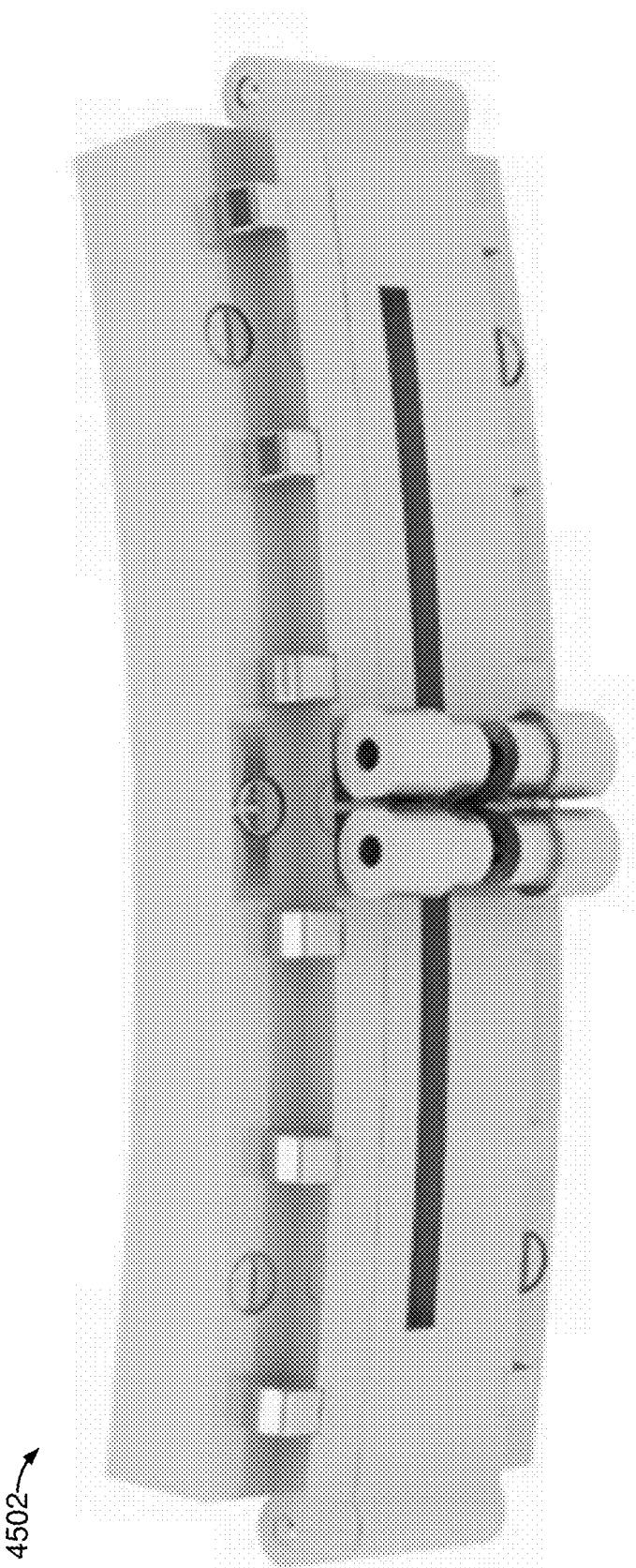
FIG. 47 is another illustration of a portion of the clasp assembly of FIG. 45.

FIG. 47 is another illustration of a portion of clasp assembly 4502.

Figure 48:
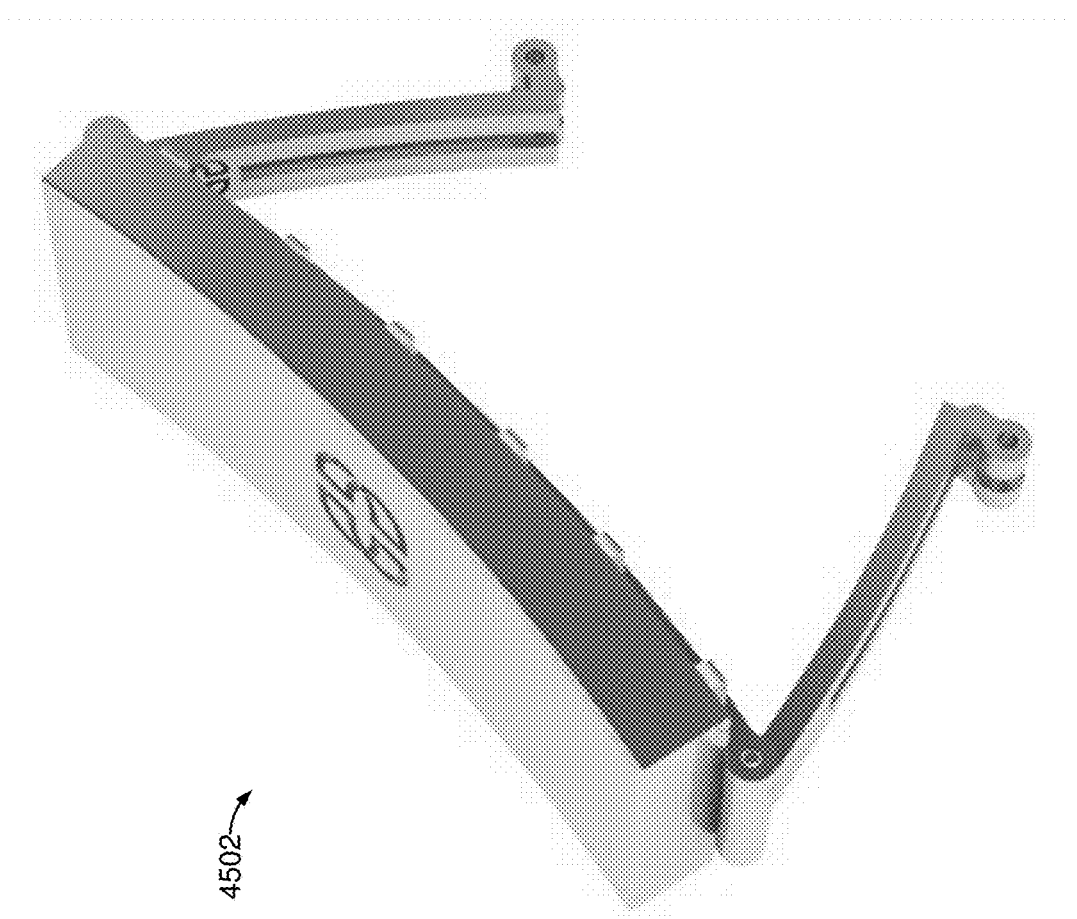
FIG. 48 is another illustration of a portion of the clasp assembly of FIG. 45.

FIG. 48 is another illustration of a portion of clasp assembly 4502.

Figure 49:
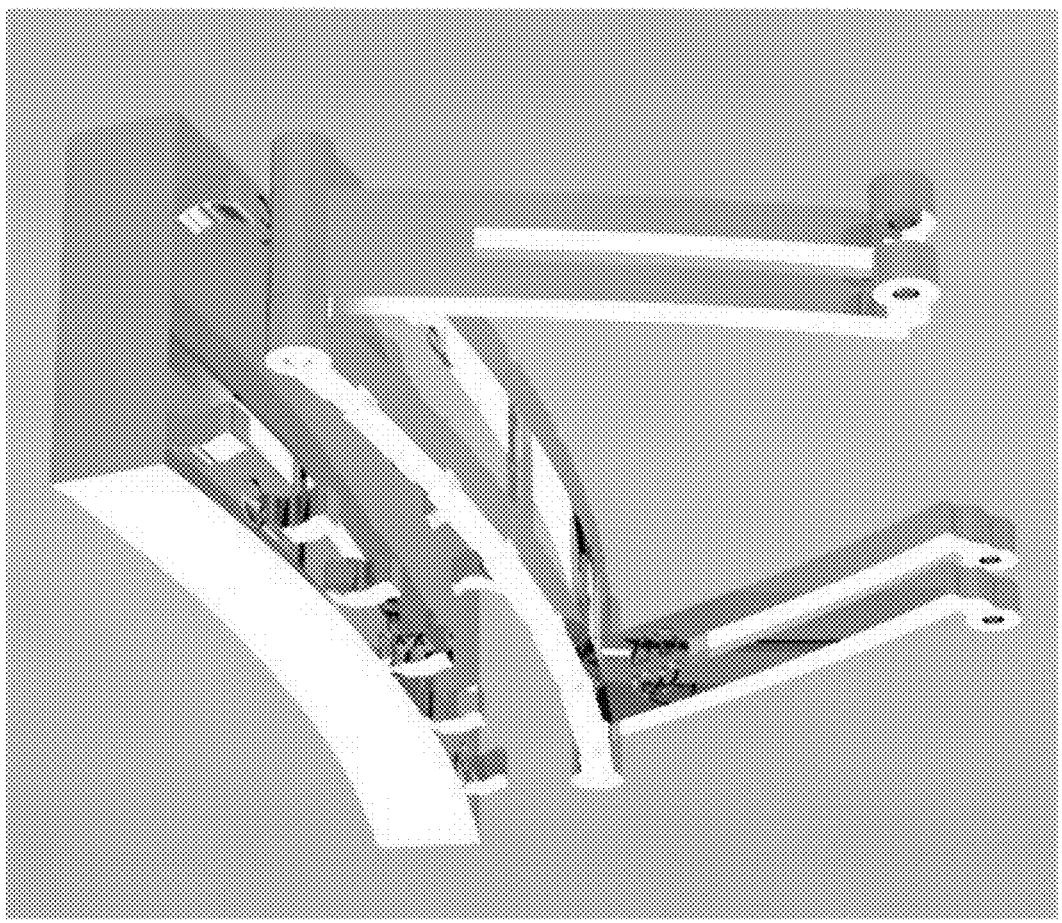
FIG. 49 is another illustration of a portion of the clasp assembly of FIG. 45.

FIG. 49 is another illustration of a portion of clasp assembly 4502.

Figure 50:
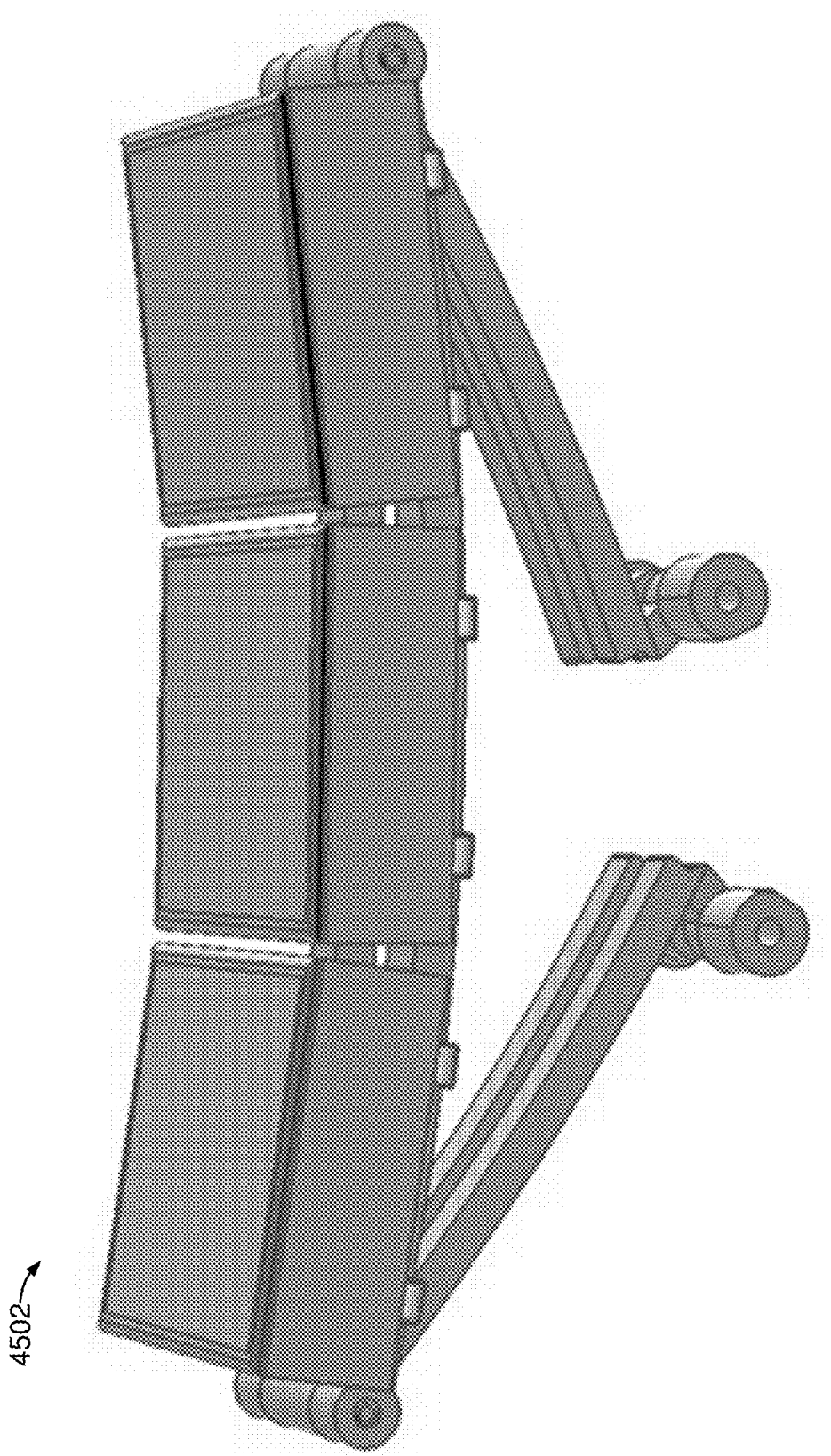
FIG. 50 is another illustration of a portion of the clasp assembly of FIG. 45.

FIG. 50 is another illustration of a portion of clasp assembly 4502.

In an embodiment, a clasp for a wearable accessory is configured to hold an electronics module, and may be further configured to replace a clasp of the wearable accessory. The clasp may be configured as one or more of a wristwatch wristband clasp, a wrist bracelet clasp, necklace/pendant clasp, a brooch clasp, and a belt clasp (e.g., a belt buckle).

A clasp may be configured as a hidden or butterfly clasp that includes a bar and two arms, where each arm has a first end hingedly coupled to a respective end of the bar and a second end to secure a respective strap of a wristband, the bar includes an inner surface to face a wrist of the wearer. A container may be configured to mount to the inner surface of the bar to maintain a surface of the container in contact with the wrist of the wearer. In an embodiment, the clasp includes a hinged cover to open outwardly from an outer surface of the clasp, away from the wrist of the wearer, to expose the cavity of the container portion, such as illustrated in FIG. 25.

Methods and systems are disclosed herein with the aid of functional building blocks illustrating functions, features, and relationships thereof. At least some of the boundaries of these functional building blocks have been arbitrarily defined herein for the convenience of the description. Alternate boundaries may be defined so long as the specified functions and relationships thereof are appropriately performed. While various embodiments are disclosed herein, it should be understood that they are presented as examples. The scope of the claims should not be limited by any of the example embodiments disclosed herein.

What is claimed is:

1. An apparatus, comprising:
    a container having a cavity therein; and
    a butterfly-type connection device configured to connect the container to a wristband such that a surface of the container is maintained in physical contact with a wearer of the wristband;
    wherein the butterfly-type connection device includes,
        a bar having multiple concave indents along each of first and second opposing edges of the bar,
        a first arm having a first end hingedly coupled to a first end of the bar, and a second end configured to couple to a first strap of the wristband, and
        a second arm having a first end hingedly coupled to a second end of the bar, and second end configured to couple to a second strap of the wristband; and
    wherein the container includes multiple tabs extending from a base portion of the container configured to engage respective ones of the concave indents of the bar to secure the container and the bar to one another.

2. The apparatus of claim 1, wherein
the first and second arms are movable between a collapsed position of the butterfly-type connection device in which the second ends of the first and second arms are drawn toward one another and pressed toward the bar to pull the first and second straps of the wristband toward one another to secure the wristband on the wrist of the wearer, and an expanded position in which a distance between the first and second straps of the wristband is expanded.

3. The apparatus of claim 1, wherein the butterfly-type connection device further includes:
    a first wristband connector configured to couple the second end of the first arm to the first strap of the wristband; and
    a second wristband connector configured to couple the second end of the second arm to the second strap of the wristband;
    wherein the first wristband connector includes a pinch portion configured to pinch the first end of the wrist strap when the butterfly-type connection device is in the collapsed position; and
    wherein the second wristband connector includes a linkage portion that includes a pin configured to couple to the second strap of the wristband.

4. The apparatus of claim 1, wherein the container is further configured to receive an electronic module within the cavity.

5. The apparatus of claim 1, wherein the container is further configured to receive a biometric sensor within the cavity to sense a biometric feature of the wearer.

6. The apparatus of claim 1, wherein the container is further configured to hold a battery within the cavity.

7. The apparatus of claim 1, further including an electronic module configured to fit within the cavity.

8. The apparatus of claim 7, wherein the electronic module includes a sensor to sense a feature at the surface of the container.

9. The apparatus of claim 7, wherein the electronic module includes a biometric sensor to sense a biometric feature of the wearer.

10. The apparatus of claim 7, wherein the electronic module includes a communication system configured to communicate with another electronic module within the container and/or a device that is external to the container.

11. The apparatus of claim 1, wherein the surface of the container has an opening to the cavity, and wherein the apparatus further includes a cover to seal the opening.

12. The apparatus of claim 11, wherein the cover is removable to permit removal and replacement of an electronic module within the cavity.

13. The apparatus of claim 11, wherein the container includes a deformable portion to releasably retain the cover over the opening, wherein the deformable portion is deformable without use of a tool.

14. The apparatus of claim 1, wherein the surface of the container is contoured to coincide with a contour of the wearer.

15. The apparatus of claim 1, wherein the butterfly-type connection device is configured to replace a butterfly connection device of the wristband.

* * * * *